United States Patent
Laurencin et al.

(10) Patent No.: US 11,946,030 B2
(45) Date of Patent: Apr. 2, 2024

(54) MULTI-CHAMBER CELL CULTURE SYSTEM

(71) Applicant: University of Connecticut, Farmington, CT (US)

(72) Inventors: Cato T. Laurencin, Farmington, CT (US); Lakshimi S. Nair, Farmington, CT (US); Mohammed Barajaa, Farmington, CT (US)

(73) Assignee: University of Connecticut, Farmington, CT (US)

( * ) Notice: Subject to any disclaimer, the term of this patent is extended or adjusted under 35 U.S.C. 154(b) by 301 days.

(21) Appl. No.: 17/124,728

(22) Filed: Dec. 17, 2020

(65) Prior Publication Data

US 2021/0189313 A1 Jun. 24, 2021

Related U.S. Application Data

(60) Provisional application No. 62/949,791, filed on Dec. 18, 2019.

(51) Int. Cl.
*C12M 1/00* (2006.01)
*C12M 1/12* (2006.01)
*C12M 1/32* (2006.01)

(52) U.S. Cl.
CPC ............ *C12M 23/34* (2013.01); *C12M 23/12* (2013.01); *C12M 37/04* (2013.01)

(58) Field of Classification Search
CPC ...... B01L 3/50; B01L 3/50255; B01L 3/5085; B01L 3/50855; G01N 21/03; G01N 2021/0346; G01N 2021/0357; C12M 23/12; C12M 23/34; C12M 25/04
See application file for complete search history.

(56) References Cited

U.S. PATENT DOCUMENTS

| | | | | |
|---|---|---|---|---|
| 2004/0214313 A1* | 10/2004 | Zhang | ................... | C12M 35/08 435/29 |
| 2005/0170498 A1* | 8/2005 | Dolley | ............... | G01N 21/0303 422/400 |
| 2019/0194588 A1* | 6/2019 | Rao | ........................ | C12M 25/14 |

OTHER PUBLICATIONS

Kovacevic, et al., Calcium-phosphate matrix with or without TGF-B3 improves tendon-bone healing after rotator cuff repair. J Sports Med. Apr. 2011; 39(4):811-9.
Kumbar, et al., Electrospun poly(lactic acid-co-glycolic acid) scaffolds for skin tis-sue engineering. Biomaterials 2008;29: 4100-4107.
Kuwahara, et al., Enzymatic crosslinking and degradation of gelatin as a switch for bone morphogenetic protein-2 activity. Tissue Eng Part A 17, 2955-2964 (2011).
Laurencin, et al., Annual review of biomedical engineering. In: Yarmush MI, editor. ( ed). Annual Reviews. Palo Alto, 1999, 19-46.
Laurencin, et al., Regenerative Engineering, 2010 Panel on the biomaterials grand challenges. J Biomed Mater Res A. Feb. 2011; 96(2):275-87.
Laurencin, et al., The ABJS Nicolas Andry Award: Tissue engineering of bone and ligament: A 15-year perspective. Clin Orthop Relat Res 2006; 447:221-236.

(Continued)

*Primary Examiner* — Dean Kwak
(74) *Attorney, Agent, or Firm* — McDonnell Boehnen Hulbert & Berghoff LLP

(57) ABSTRACT

System and methods for the culturing of multiple independent cell types under uniform conditions.

19 Claims, 18 Drawing Sheets

(56) References Cited

OTHER PUBLICATIONS

Laurencin, et al., Regenerative engineering: approaches to limb regeneration and other grand challenges. Regenerative Engineering and Translational Medicine. 2015; 1: 13.
Laurencin, et al., "The Quest toward Limb Regeneration: A Regenerative Engineering Approach." Regenerative Biomaterials, vol. 3, Issue 2, Jun. 1, 2016, pp. 123-125.
Lee, et al., Growth factor delivery-based tissue engineering: general approaches and a review of recent developments. J R Soc Interface 8, 153-170 (2011).
Li, et al. Mechanism of Human Dermal Fibroblast Migration Driven by Type I Collagen and Platelet-derived Growth Factor-BB. Mol Biol Cell 15, 294-309 (2004).
Lin, et al., Trans differentiation of myoblasts into osteoblasts—possible use for bone therapy. J. Pharm. Pharmacol. 69, 1661-1671 (2017).
Liu, et al., Electrospun nanofibers for wound healing. Materials Science and Engineering: C 76, 1413-1423 (2017).
Lu, et al., Anterior cruciate ligament regeneration usingbraided biodegradable scaffolds: In vitro optimization studies. Biomaterials 2005;26: 4805-4816.
Lu, et al., In vitro bone formation using muscle-derived cells: A new paradigm for bone tissue engineering using polymer bone morphogenetic protein matrices. Biochem Biophys Res Commun 2003; 305:882-889.
Lu, et al. Coaxial electrospun fibers: applications in drug delivery and tissue engineering. Wiley Interdiscip Rev Nanomed Nanobiotechnol 8, 654-677 (2016).
Lynch, et al. Effects of the platelet-derived growth factor/insulin-like growth factor-I combination on bone regeneration around titanium dental implants. Results of a pilot study in beagle dogs. J. Periodontol. 62, 710-716 (1991).
Lyon, et al., Ultrastructural differences between the cells of the medical collateral and the anterior cruciate ligaments. Clin. Orthop. Relat. Res. 279-286 (1991).
Ma, et al., Surface engineering of electrospun polyethylene terephthalate (PET) nanofibers towards development of a new material for blood vessel engineering. Biomaterials 26, 2527-2536 (2005).
McCusker, et al., The axolotl model for regeneration and aging research: a mini-review. Gerontology. 201 I; 57 (6):565-71.
McCusker, et al., The axolotl limb blastema: cellular and molecular mechanisms driving blastema formation and limb regeneration in tetrapods. Regeneration 2, 54-71 (2015).
Miller, et al., Common themes in tetrapod appendage regeneration: a cellular perspective. EvoDevo 10, 11 (2019).
Mishra, et al., (2011) Chemokines at the crossroads of tumor fibroblast interactions that promote malignancy. Journal of leukocyte biology 89: 31-39.
Molloy, et al., The roles of growth factors in tendon and ligament healing. Sports Med. 2003;33(5):381-94.
Moradi, et al., The potential role of regenerative medicine in the management of traumatic patients. J. Inj. Violence Res. 7, 27-35 (2015).
Munoz-Pinto, et al., Inorganic-organic hybrid scaffolds for osteochondral regeneration. J Biomed Mater Res A. Jul. 2010; 94(1):112-21.
Murphy, et al., Mesenchymal stem cells: Environmentally responsive therapeutics for regenerative medicine. Experimental and Molecular Medicine. 2013.
Myllyla, et al., Bone morphogenetic proteins 4 and 2/7 induce osteogenic differentiation of mouse skin derived fibroblast and dermal papilla cells. Cell Tissue Res. 355, 463-470 (2014).
Nam, et al. (2013) Reprogramming of human fibroblasts toward a card1ac fate. Proc Natl Acad Sci USA 110(14):5588-5593.
Pang, et al. (2011) Induction of human neuronal cells by defined transcription factors. Nature 476(7359):220-223.
Park, et al., Predictors of glass transition in the biodegradable poly-lactide and poly-lactide-co-glycolide polymers. Journal of Applied Polymer Science 100, 1983-1987 (2006).
Patel, et al. Integrating soft and hard tissues via interface tissue engineering. J. Orthop. Res. 36, 1069-1077 (2018).
Pirraco, et al., Fibroblasts regulate osteoblasts through gap junctional communication. Cytotherapy 14, 1276-1287 (2012).
Ruijtenberg, et al., Coordinating cell proliferation and differentiation: Antagonism between cell cycle regulators and cell type-specific gene expression. Cell Cycle 15, 196-212 (2016).
Sahoo, et al., Growth factor delivery through electrospun nanofibers in scaffolds for tissue engineering applications. J Biomed Mater Res A 93, 1539-1550 (2010).
Saveh-Shemshaki, et al., Nanofiber-based matrices for rotator cuff regenerative engineering. Acta Biomater 94, 64-81 (2019).
Seki, et al., (2011) Direct conversion of mouse fibroblasts to hepatocyte-like cells by defined factors. Nature 475 (7356):390-393.
Seluanov, et al., Establishing Primary Adult Fibroblast Cultures From Rodents. J Vis Exp (2010) doi: 10.3791/2033.
Si, et al., The biological effects of recombinant human bone morphogenetic protein 2 on human periodontal ligament fibroblasts. Hua Xi Kou Qiang Yi Xue Za Zhi 20, 10-13 (2002).
Sidney, et al., Effect of culture medium on propagation and phenotype of corneal stroma-derived stem cells. Cytotherapy. Dec. 2015; 17(12):1706-22. doi: 10.1016/j.jcyt.2015.08.003. E pub Oct. 9, 2015.
Spalazzi, et al. In vivo evaluation of a multiphased scaffold designed for orthopedic interface tissue engineering and soft tissue-to-bone integration. J Biomed Mater Res A. Jul. 2008;86(1):1-12.
Spalazzi, et al., Development of controlled matrix heterogeneity on a triphasic scaffold for orthopedic interface tissue engineering. Tissue Eng. 12, 3497-3508 (2006).
Stern, et al. Isolation and culture of primary osteocytes from the long bones of skeletally mature and aged mice. BioTechniques 52, 361-373 (2012).
Szabo, et al., (2010) Direct conversion of human fibroblasts to multilineage blood progenitors. Nature 468 (7323):521-526.
Tanaka, et al. Involvement of the osteoinductive factors, Tmem119 and BMP-2, and the ER stress response PERK-elF2α-ATF4 pathway in the commitment of myoblastic into osteoblastic cells. Calcif. Tissue Int. 94, 454-464 (2014).
Thier M, et al. (2012) Direct conversion of fibroblasts into stably expandable neural stem cells. Cell Stem Cell 10 (4):473-479.
Velve-Casquillas, et al. "Microfluidic Tools for Cell Biological Research." Nano today 5.1 (2010): 28-47. PMC. Web. Nov. 1, 2017.
Wada, et al. (2013) Induction of human cardiomyocyte-like cells from fibroblasts by defined factors. Proc Natl Acad Sci USA 110(31):12667-12672.
Wang, et al., Role of osteoblast-fibroblast interactions in the formation of the ligament-to-bone interface. J. Orthop. Res. 25, 1609-1620 (2007).
Wang, et al. Novel biomaterial strategies for controlled growth factor delivery for biomedical applications. NPG Asia Mater. 9, e435-e435 (2017).
Amini, et al., Optimally Porous and Biomechanically Compatible Scaffolds for Large-Area Bone Regeneration. Tissue Eng Part A 18, 1376-1388 (2012).
Asamura, et al., Bone regeneration using a bone morphogenetic protein-2 saturated slow-release gelatin hydrogel sheet: evaluation in a canine orbital floor fracture model. Ann Plast Surg 64, 496-502 (2010).
Bayrak, E. & Yilgor Huri, P. Engineering Musculoskeletal Tissue Interfaces. Front. Mater. 5, (2018).
Borden, et al., The sintered microsphere matrix for bone tissue engineering: in vitro osteoconductivity studies. J. Biomed. Mater. Res. 61, 421-429 (2002).
Boys, et al., Next generation tissue engineering of orthopedic soft tissue-to-bone interfaces. MRS Commun. 7, 289-308 (2017).
Buzgo, et al., Blend electrospinning, coaxial electrospinning, and emulsion electrospinning techniques. in Core-Shell Nanostructures for Drug Delivery and Theranostics (eds. Focarete, M. L. & Tampieri, A.) 325-347 (Woodhead Publishing, 2018). doi:10.1016/B978-0-08-102198-9.00011-9.
Canalis, et al., Effects of platelet-derived growth factor on bone formation in vitro. Journal of Cellular Physiology 140, 530-537 (1989).

(56) References Cited

OTHER PUBLICATIONS

Canalis, et al., Growth Factors and Cytokines in Bone Cell Metabolism, Annual Review of Medicine 1991, 42:1, 17-24.
Chiarello, et al., Aging Clin Exp Res. Oct. 2013; 25 Suppl 1: S 101-3. doi: 10.1007/s40520-0I 3-0088-8. Epub Sep. 18, 2013.
Cines, et al. Endothelial cells in physiology and in the pathophysiology of vascular disorders. Blood 91, 3527-3561 (1998).
Clark, et al., TGF-beta 1 stimulates cultured human fibroblasts to proliferate and produce tissue-like fibroplasia: a fibronectin matrix dependent event. J Cell Physiol. Jan. 1997; 170(1):69-80.
Cooper, et al., Evaluation of the anterior cruciate ligament, medial collateral ligament, achilles tendon and patellar tendon as cell sources for tissue-engineered ligament. Biomaterials 2006; 27:2747-2754.
Cooper, et al., Biomimetic tissue-engineered anterior cruciate ligament replacement. Proc Natl Acad Sci USA 2007; 104:3049-3054.
Cooper, et al., Fiber-based tissue-engineered scaffold for ligament replacement: Design considerations and in vitro evaluation. Biomaterials 2005; 26: 1523-1532.
Cross, et al., Growth factors in development, transformation, and tumorigenesis. Cell 64, 271-280 (1991).
Cushnie, et al., Amorphous hydroxyapatite-sin-tered polymeric scaffolds for bone tissue regeneration: Physicalcharacterization studies. J Biomed Mater Res 2008; 84:54-62.
Cushnie, et al., Tissue engineered matrices as functional delivery systems: Adsorption and release of bioactive proteins from degradable composite scaffolds. J Biomed Mater Res A 2010; 94:568-575.
Daskalaki, Andriani. Medical Advancements in Aging and Regenerative Technologies: Clinical Tools.
Echave, et al., Gelatin as Biomaterial for Tissue Engineering. Curr. Pharm. Des. 23, 3567-3584 (2017).
Gamal, et al., Human periodontal ligament fibroblast response to PDGF-BB and IGF-1 application on tetracycline HCI conditioned root surfaces. J. Clin. Periodontol. 25, 404-412 (1998).
Gardiner DM, Towards a functional analysis of limb regeneration. Semin Cell Dev Biol. Aug. 1999; 10(4):385-93.
Gentile, et al., An Overview of Poly(lactic-co-glycolic) Acid (PLGA)-Based Biomaterials for Bone Tissue Engineering. Int J Mol Sci 15, 3640-3659 (2014).
Grazul-Bilska, et al., Wound healing: the role of growth factors. Drugs Today 39, 787-800 (2003).
Gu, et al. "3-Dimensional Bioprinting for Tissue Engineering Applications." Biomaterials Research 20 (2016): 12. PMC. Web. Nov. 1, 2017.
Han, et al. (2012) Direct reprogramming of fibroblasts into neural stem cells by defined factors. Cell Stem Cell 10 (4):465-472.
Hee, et al., Influence of three-dimensional scaffold on the expression of osteogenic differentiation markers by human dermal fibroblasts. Biomaterials. Feb. 2006:27(6):875-84. Epub Aug. 1, 20055.
Hee, et al., Endogenous bone morphogenetic proteins mediate I alpha, 25-dihydroxyvitamin D (3)-induced expression of osteoblast differentiation markers in human dermal fibroblasts. J Orthop Res. Feb. 2009;27(2):162-8. doi: 10.1002/ior.20728.
Hiramatsu, et al. (2011) Generation of hyaline cartilaginolous tissue from mouse adult dermal fibroblast culture by defined factors. J Clin Invest 121(2):640-657.
http://blogs.rsc.org/chipsandtips/2006/10/23/rapid-curing-of-pdms-for-microfluidic-applications/.
http://kirschner.med.harvard.edu/files/bionumbers/fundamentalBioNumbersHandout.pd.
http://www.woundsource.com/blog/difference-between-acute-and-chronic-wounds.
https://www.woundcarecenters.org/article/wound-basics/ different-types-of-wounds.

Huang, et al. (2011) Induction of functional hepatocyte-like cells from mouse fibroblasts by defined factors. Nature 475 (7356):386-389.
Ieda, et al. (2010) Direct reprogramming of fibroblasts into functional cardiomyocytes by defined factors. Cell 142 (3):375-386.
Ikada, et al., Protein release from gelatin matrices. Adv. Drug Deliv. Rev. 31, 287-301 (1998).
Inagawa, et al., (2013) Direct reprogramming of mouse fibroblasts into cardiac myocytes. J Cardiovasc Transl Res 6 (1):37-45.
Jabbarzadeh, et al., Apatitenano-crystalline surface modification of poly(lactide-co-glycolide) sintered microsphere scaffolds for bone tissue engineering: Implications for protein adsorption. J Biomater Sci Polymer Ed 2007; 18:1141-1152.
Janardhanan, et al., Co-culture Strategies in Bone Tissue Engineering: The Impact of Culture Conditions on Pluripotent Stem Cell Populations. Tissue Eng Part B Rev 18, 312-321 (2012).
Jiang, et al., Functionalization of chitosan/poly (lactic acid-glycolic acid) sinteredmicrosphere scaffolds via surface heparinization for bone tissue engineering. J Biomed Mater Res A 201 O; 93: 1193-1208.
Jiang, et al., Chitosan-poly(lactide-co-glycolide) microsphere-based scaffolds for bone tissue engineering: in vitro degradation and in vivo bone regeneration studies. Acta Biomater 6, 3457-3470 (2010).
Karalaki, et al., Muscle regeneration: cellular and molecular events. In Vivo. Sep.-Oct. 2009;23(5):779-96.
Katti, et al., Bioresorbable nanofiber-based systems for wound healing and drug delivery: optimization of fabrication parameters. J. Biomed. Mater. Res. Part B Appl. Biomater. 70, 286-296 (2004).
Kerstin, et al., Dermal fibroblasts derived from fetal and postnatal humans exhibit distinct responses to insulin like growth factors. BMC Developmental Biology20077: 124.
Khan, et al, In situ synthesized ceramic-polymer composites for bone tissue engineering: Bioactivity and degradation studies. J Mat Sci 2007; 42:4183-4190.
Khan, et al., . Tissue engineering of bone: Material and matrix considerations. J Bone Joint Surg 2008; 90:36-42.
Kim, et al., (2012) Direct lineage reprogramming to neural cells. Curr Opin Neurobiol 22(5):778-784.
Kobayashi, et al., Effect of insulin-like growth factor 1 and basic fibroblast growth factor on DNA synthesis and collagen production in cultured anterior cruciate ligament cells. J Orthop Sci 2, 349-356 (1997).
Kofron et al., Novel tubular composite matrix for bone repair. J Biomed Mater Res A 2007; 82:415-425.
Kofron, et al., Development of a calcium phosphatecoprecipitate/ poly(lactide-co-glycolide) DNA delivery system: release kinetics and cellular transfection studies. Biomaterials2004; 25:2637-2643.
Kostrominova, et al., Ultrastructure of myotendinous junctions in tendon-skeletal muscle constructs engineered in vitro. Histol Histopathol. 2009; 24:541-550.
Yamamoto, et al., Direct conversion of human fibroblasts into functional osteoblasts by defined factors. Proc Natl Acad Sci U S A. May 12, 2015;112(19):6152-7. Epub Apr. 27, 2015.
Yamamoto, et al., Controlled release of growth factors based on biodegradation of gelatin hydrogel. J Biomater Sci Polym Ed 12, 77-88 (2001).
Yang, et al. Bone morphogenetic proteins: Relationship between molecular structure and their osteogenic activity. Food Science and Human Wellness 3, 127-135 (2014).
Yao, et al., Animal-cell culture media: History, characteristics, and current issues. Reprod Med Biol 16, 99-117 (2017).
Yu, et al., Effect of EGF and bFGF on fibroblast proliferation and angiogenic cytokine production from cultured dermal substitutes. J Biomater Sci Polym Ed.2012;23(10):1315-24. Epub May 8, 2012.
Yun, Changes in Regenerative Capacity through Lifespan. Ed. Francese Cebria. International Journal of Molecular Sciences 16.10 (2015): 25392-25432. PMC. Web. Nov. 4, 2017.

* cited by examiner (A) Each region is incorporated with a tissue-mediator growth factor (B) Each region is populated with its respective cell type, and cultured separately for 2 days to allow for complete adherence (C) 2 days post-initial culture, regions are harvested and assessed for CGS development (D) CGS is further cultured for 3 and 7 days

MULTI-CHAMBER CELL CULTURE SYSTEM

CROSS REFERENCES

This application claim priority to U.S. Provisional Patent Application Ser. No. 62/949,791 filed Dec. 18, 2019, incorporated by reference here in its entirety.

STATEMENT OF GOVERNMENT SUPPORT

This disclosure was made with government support under Grant AR068147 from the National Institutes of Health. The government has certain rights in the disclosure.

BACKGROUND

Cells behaviors are strongly influenced by the extracellular environment, which include both the extra-cellular milieu and the relationship with surrounding cell populations. The ability to study such behaviors in vitro is determined by the experimental set-up, which therefore needs to be given careful consideration and needs to reflect the in vivo environment to the extent possible. Most of the interactions that happen within the body at the cellular level take place between more than two populations of cells.

SUMMARY DISCLOSURE

In a first aspect, the disclosure provides a cell culture system comprising a culture plate comprising at least one well, which comprises a bottom and wall; and one or more branched inserts, wherein each well contains no more than one branched insert. The branched insert comprises three or more branches; divides a bottom portion of the well into three or more chambers; and forms a non-permeable seal with the bottom of the well and the bottom portion of the wall of the well.

In a second aspect, the disclosure provides a branched insert comprising polydimethylsiloxane (PDMS); wherein the branched insert comprises three or more branches.

In a third aspect, the disclosure provides a method for culturing multiple cell populations comprising adding culture media and a cell population into each individual chamber in a single well of the system of the first aspect; and incubating the culture plate.

DETAILED DESCRIPTION

In a first embodiment, the disclosure provides a system for culturing multiple cell populations. The system comprises a culture plate comprising at least one well, and one or more branched inserts. The branched insert comprises three or more branches; divides the bottom portion of a well into three or more chambers; and forms a non-permeable seal with the bottom and the bottom portion of the wall of the well.

As used herein, a "cell population" is defined as the population of cells present in a single chamber and can be any group or type of biological cells suitable for use in cell culture. A cell population can include only one type of cell or can include a mixture of different cell types. Multiple cell populations can include different "cell populations" or more than one of the same "cell population."

As used herein the culture plate is a plate containing at least one well and suitable for use in biological cell-culture. The culture plate can contain any number of wells including but not limited to 1, 2, 3, 4, 5, 6, 7, 8, 9, 10, 11, 12, 13, 14, 15, 16, 17, 18, 19, 20, 21, 22, 23, 24, or more wells. The well can be any size suitable for use in the present disclosure. In various embodiments, the culture plate can be any commercially available culture plate, including, but not limited to a 6-well, a 12-well, a 24-well plate, a 36-well plate, a 48-well plate, or a 96-well plate. In another embodiment the culture plate can be custom made and comprise at least one well.

As used herein the one or more branched inserts are any insert, which fits into the well of the culture plate, and is branched. Each well can comprise no more than one insert. If the culture plate contains 6 wells, the system comprises 6 inserts and each well contains one insert. The insert comprises at least three branches but can comprise more than three branches. In various embodiments, each insert may independently comprise 4, 5, or 6 branches. In one embodiment, each insert comprises the same number of branches.

When the insert is present inside the well, the bottom portion of the well is divided into three or more chambers. The number of chambers in the bottom portion of each well is determined by the number of branches on the individual insert present in the well. Thus, if the insert comprises 4 branches, it divides the bottom portion of the well into 4 chambers. In various embodiments, the bottom portion of each well is independently divided into 3, 4, 5, or 6 chambers. In one embodiment, the bottom portion of each well is divided in the same number of chambers. In another embodiment, the branched insert divides the bottom portion of the well into chambers that are identical in volume, dimensions and geometry. As used herein, "volume" is the three-dimensional space of the chamber and limits the maximum amount of liquid which can be added to the chamber. As used herein, "dimension" is the size of the chamber and "geometry" is the shape of the chamber.

Figure 18:
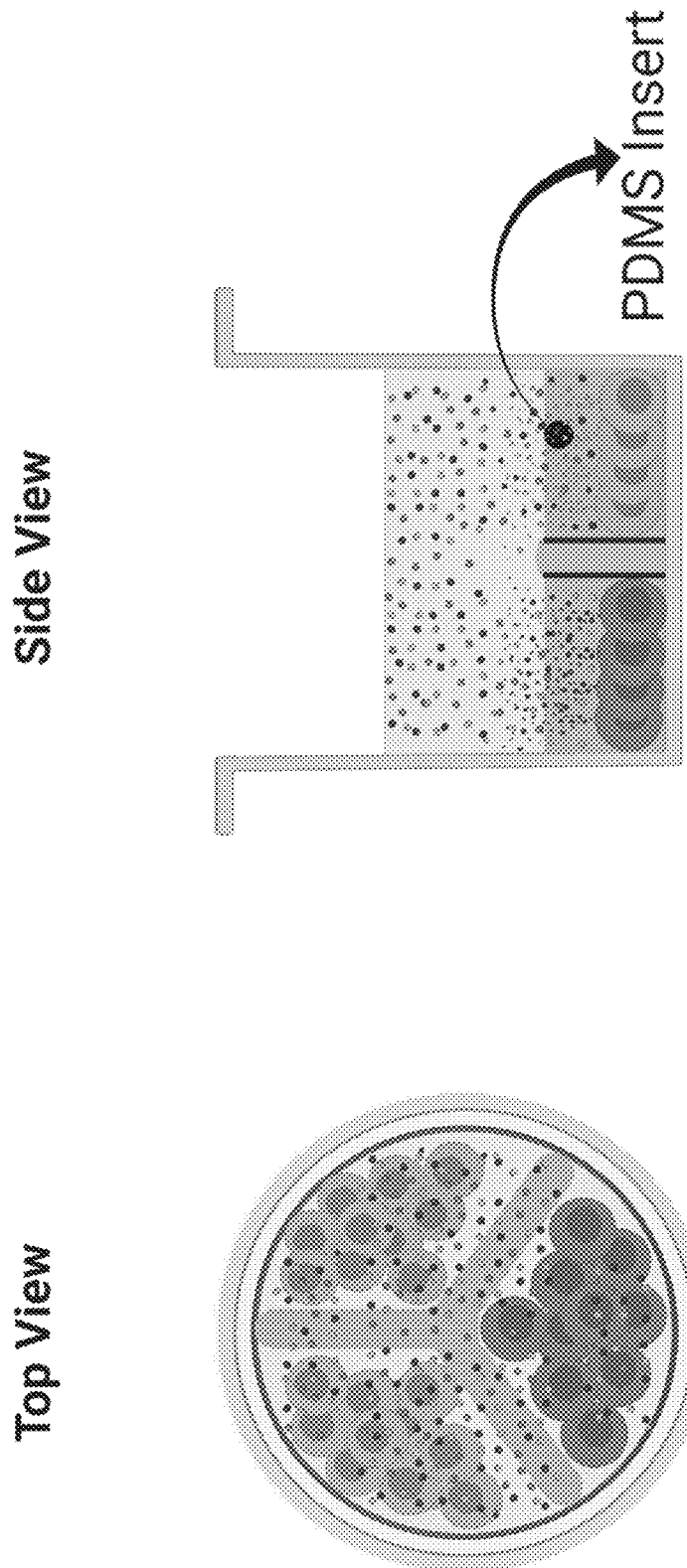
FIG. 18 shows an embodiment of the disclosure and how it can be utilized to physically separate seeded cells into individual chambers, while also permitting media to be shared by the cells in the separate chambers.

As used herein "bottom portion" means that the insert does not divide the well into chambers along the entire height of the well, but instead divides a bottom portion of the well into non-permeable chambers, while the top portion of the well remains un-divided (see, for example, FIG. 18). The insert forms a non-permeable seal with the bottom of the well and the bottom portion of the wall of the well. The bottom portion can be defined as any portion of the well starting from the bottom of the well and extending upwards, but must be less than half the full height of the well. In non-limiting examples, the bottom portion of the well can be the bottom ⅔, ⅓, or ½ of the well height. The non-permeable seal between the insert and the bottom of the well and the bottom portion of the wall of the well prevents the migration of cells. In one embodiment, the insert is non-permanent and removable from the well. In another embodiment, the insert is permanently integrated into the well and cannot be removed. When the insert is permanently integrated into the well, the insert comprises any material that is normally found in culture plates, including, but not limited to polystyrene The culture plate can comprise any material normally found in culture plates, including, but not limited to polystyrene.

In another embodiment, the insert may be a removable, non-permanent insert, which can comprise any material suitable for use in the system that can form a non-permeable seal between the insert and the bottom and wall of the well, including but not limited to a cured polymer. One, non-limiting, example of a cured polymer is polydimethylsiloxane (PDMS). In one embodiment, the insert forms a non-permeable seal by adhering to the bottom and wall of the well. As used herein "adhere" is defined as sticking to the bottom of the well and the bottom portion of the wall of the well in order to form a temporary, impenetrable bond with the parts of the well which make contact with the insert.

In a second aspect, the disclosure provides a branched insert comprising polydimethylsiloxane (PDMS); wherein the branched insert comprises three or more branches.

Various embodiment of the branched insert are outlined above and include an insert comprising 3, 4, 5, 6, or more branches.

In a third aspect, the disclosure provides a method for culturing multiple cell populations under uniform conditions comprising adding culture media and a cell population into each individual chamber in a well of the system of the first aspect; and incubating the culture plate.

The disclosed novel systems and methods allow researchers to study the cellular behavior and interactions between multiple populations of cells in the absence of physical contact between the cells. The non-permeable insert divides the bottom portion of the well into chambers and extends high enough up the wall of the well to prevent cells seeded in one chamber from physically contacting the cells seeded in the other chambers. Use of the novel multi-chamber cell culture system provides a method for studying the behavior of a single cell population in a multi-chamber environment when grown with two, or more, other populations of cells. Furthermore, in the present invention, each cell population can be cultured under uniform conditions. Uniform conditions can refer to the physical characteristics of the chambers, so that each chamber has identical volume, dimensions, and geometry.

In one embodiment the non-permeable branched insert extends high enough up the wall of the well, so that it can also prevent media from each chamber from mixing. In this embodiment, the amount of media added to each individual chamber does not fill the entire volume of the individual chambers in the bottom portion of well and the media and cell are confined to an individual chamber. The methods according to this embodiment can be used to culture different cell populations in the same media in each chamber or different cell populations in different media in each chamber.

The method can comprises culturing three different cell populations, with the same media in each chamber, so that the well comprises three different chambers each with a different cell population in media. The culture plate is then incubated. This allows for the culturing of different cell populations under uniform conditions. The insert in this embodiment, prevents the migration of cells and media between the individual chambers of the well, including adjacent chambers. In one, non-limiting example, the method can be used to investigate the most suitable growth medium to sustain growth of different cell populations. In another example, methods according to this embodiment can be used to culture the same cell population in each chamber but in different media in each chamber to investigate the effects of different media on the same type of cell population under uniform conditions. In a further example, the method of this embodiment can be used to culture the same cell population and the same media in each chamber, but with the addition of different test compounds to each chamber.

In a second, non-limiting embodiment, the non-permeable insert is high enough to prevent the seeded cells in each chamber from physically contacting each other, but the amount of media added exceeds the volume of the chambers and overfills the insert.

As used herein, "overfill" means that the media fills each chamber completely and then fills more of the well above the chambers, so that the bottom portion of the well and at least part of the top portion of the well is filled with media. This embodiment permits each chamber to be contacted by the same media and allows compounds secreted or released by a cell population in one chamber, to enter the general media and contact the other cell populations in the other chambers. According to the methods of this embodiment, interactions between the cell populations in the separate chambers are limited to chemical signaling, which can facilitate the research of more complex cellular relationships in a cell-culture environment.

The ability to culture multiple cell populations, while preventing physical interactions between the cell populations, provides novel methods for studying natural non-physical interactions between cell populations and can result in improved culturing success for certain cell populations that require the co-culturing of support cells, but not physical contact. Furthermore, such novel methods can assist in identifying and establishing synthetic interactions between multiple cell populations. Further examples of uniform conditions according to this embodiment can also include the external environment of the cell population. The external environment can include, but is not limited to the culture media, cellular signaling molecules released by the cell populations and incubation protocol(s). Since the cells populations are being cultured in the same well but physically being separated, they can share the same medium and be exposed to the cellular signaling molecules released by the other cell populations in the neighboring chambers, which can initiate their interactions through paracrine signaling. In addition, the different cell populations are cultured under identical and uniform conditions within the same well to ensure that any cellular behaviors are to be observed during the culture time are likely to be due to the effects of multi-culture environment and not due to other factors (including non-uniformity in chamber volume, dimensions or geometry). In one example of this embodiment, the system and methods of the disclosure were used to culture skin fibroblasts (SFs), soft tissue fibroblasts (STFs) and osteoblasts (OBs) in the same well, each in its own chamber. This was repeated in multiple wells in a culture plate.

Different types of growth medium were then added to each of the multiple wells to investigate the most suitable growth medium to sustain the growth of the different cell populations when cultured together in the same well as opposed to the same cell populations being each single cultured, alone, in its own well in the growth mediums. This allowed optimizing the most suitable growth medium to sustain the growth of the three different cell populations when cultured together. In addition, the system and methods allowed studying the growth behavior of each of the different cell populations during tri-culture, as the tri-cultured cell populations resulted in up-normality in proliferation rates when cultured together as opposed to culturing them alone, regardless of the type of medium they were cultured in. Thus, any changes in cellular behavior are due to the effects of the paracrine interactions and/or the chemical cues released by the cells and not due to the type of culture medium used.

As used herein the culture media can be any media suitable for use in the culturing of cell. In various embodiments, the same media can be added to each chamber or each chamber can have different media.

While the disclosure has been described with reference to preferred embodiments, it will be understood by those skilled in the art that various changes may be made and equivalents may be substituted for the elements thereof without departing from the scope of the disclosure. In addition, many modifications may be made to adapt the teaching of the disclosure to particular use, application, manufacturing conditions, use conditions, composition, medium, size, and/or materials without departing from the essential scope and spirit of the disclosure. Therefore, it is intended that the disclosure not be limited to the particular embodiments and best mode contemplated for carrying out this disclosure as described herein. Since many modifications, variations, and changes in detail can be made to the described examples, it is intended that all matters in the preceding description and shown in the accompanying figures be interpreted as illustrative and not in a limiting sense.

Chemical compounds are described using standard nomenclature. For example, any position not substituted by any indicated group is understood to have its valency filled by a bond as indicated, or a by hydrogen atom.

All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and words of a similar nature in the context of describing the improvements disclosed herein (especially in the context of the following claims) are to be construed to cover both the singular and the plural, unless otherwise indicated herein or clearly contradicted by context. Further, the terms "first," "second," and the like herein do not denote any order, quantity, or relative importance, but rather are used to distinguish one element from another.

All methods described herein can be performed in any suitable order unless otherwise indicated herein or otherwise clearly contradicted by context. The use of any and all examples, or exemplary language (e.g., "such as"), is intended merely to better illustrate the disclosure and does not pose a limitation on the scope of the disclosure or any embodiments unless otherwise claimed.

EXAMPLE

In Vitro Tri-Culture Study for the Determination of a Heterogenic Culture Medium: A Proof of Design Study.

After fabricating, testing and confirming the functionality of the disclosed tri-culture system it was used for an actual in vitro experiment that was conducted in ordered to evaluate the cellular behavior (proliferation) of three different populations of cells grown together in different growth medium as described below: This study represents an example of the utility of the disclosed multi-chamber cell-culture system.

in both conditions, the SCE and TCE, was examined using an MTS assay kit following the manufacturer's instructions. At predetermined time points, 3 and 7 days, mediums were removed and cells were washed with PBS. A 200 µL cocktail solution of MTS reagent premixed with the corresponding medium type at a ratio of (1:5) was added to every chamber, followed by incubation for 3 hours at 37° C. in the dark. Next, 100 µL from each chamber was collected and transferred to a 96-well plate and the absorbance was measured at 490 nm. Data were presented as the average increase in the fold between day 3 and day 7 of three experimental replicates for every cell type cultured in every medium in each condition.

TABLE 1

The developed tri-culture system was utilized to determine a heterogeneous optimal growth medium that would sustain the growth of the three different cell types in a tri-culture environment.

| Condition Cell type | Different types of growth mediums | | | | | |
|---|---|---|---|---|---|---|
| | SFs medium | | STFs medium | | OBs medium | |
| | TCE | SCE | TCE | SCE | TCE | SCE |
| SFs | 0.91 ± 0.01 | ****1.52 ± 0.01 | 0.44 ± 0.03 | ****1.12 ± 0.02 | 1.62 ± 0.05 | ***1.94 ± 0.02 |
| STFs | 1.04 ± 0.05 | ***1.69 ± 0.05 | 0.79 ± 0.24 | *1.33 ± 0.24 | 1.23 ± 0.11 | **1.71 ± 0.12 |
| OBs | *1.56 ± 0.21 | 1.12 ± 0.17 | *1.15 ± 0.04 | 0.64 ± 0.2 | *2.41 ± 0.51 | 1.44 ± 0.18 |

| Condition Cell type | Different compositions of SFs, STFs, OBs growth mediums | | | | | | | |
|---|---|---|---|---|---|---|---|---|
| | [2:1:1] | | [1:2:1] | | [1:1:2] | | [1:1:1] | |
| | TCE | SCE | TCE | SCE | TCE | SCE | TCE | SCE |
| SFs | 1.01 ± 0.17 | **1.61 ± 0.06 | 0.65 ± 0.1 | ***1.29 ± 0.05 | 1.42 ± 0.07 | **1.92 ± 0.07 | 0.99 ± 0.2 | *1.48 ± 0.06 |
| STFs | 1.31 ± 0.12 | *1.61 ± 0.07 | 0.84 ± 0.28 | *1.48 ± 0.08 | 0.87 ± 0.17 | *1.22 ± 0.56 | 1.02 ± 0.12 | *1.5 ± 0.3 |
| OBs | *1.67 ± 0.31 | 0.97 ± 0.22 | *1.24 ± 0.31 | 0.61 ± 0.17 | **1.99 ± 0.2 | 1.31 ± 0.06 | *1.82 ± 0.17 | 1.2 ± 0.3 |

Methods:
Development of the Tri-Culture System.

To optimize an optimal growth medium for a heterogeneous culture, the different cell phenotypes were cultured either alone (single culture environment (SCE)) or together (tri-culture environment (TCE)) in different types of mediums; (1) SFs medium [MEM supplemented with 10% FBS, 1% P/S], (2) STFs medium [DMEM: F-12 supplemented with 10% FBS and 1% P/S, (3) OBs medium [MEM–α(1×) supplemented with 10% FBS and 1% P/S], (4)[2:1:1], (5)[1:2:1], (6) [1:1:2], and (7) [1:1:1], respectively (n=3 for every cell phenotype/medium type/condition). For culturing the cells in the TCE, autoclaved PDMS inserts were introduced into the bottom of the 24-well plates. Next, a 200 µL cell suspension of every cell type in the corresponding medium was added to every chamber at a concentration of $25 \times 10^3$/mL (5 k cells/chamber/cell type). For culturing the cells in the SCE the same procedure was completed expect for that a single chamber of every well was only occupied by a single cell population. Plates were incubated at 37° C. and 5% $CO_2$ for 24 hours to allow cells to completely adhere to their respective chambers, followed by the addition of 400 µl (800 µl in the case of SCE) of the corresponding medium type to each well to bring the total volume to 1 mL/well. Mediums were change every days. The growth of the cells The data from Table 1 indicate that osteoblasts (OBs) medium provided an optimal growth medium for the three different cell types in a tri-culture environment. Numbers indicate the average increase in fold of three repeated experiments between days 3 and 7 (n=3 per every experiment and n=9 per fold number; Student t-test, *P<0.05, P<0.01, *P<0.001, ****P<0.0001 compared to the TCE or SCE for the same cell and medium types).

Results:

To examine the most suitable growth medium that would best sustain the growth of the three different cell types both in the SCE and TCE, cells were seeded and assayed for proliferation after 3 and 7 days post culture. Data indicate that osteoblasts (OBs) medium provided an optimal growth medium for the three different cell types in both the SCE and TCE (Table 1 and FIG. 15). Regardless of the medium type, all the three different cell types showed up-normality in cell proliferation in the TCE compared to their proliferation in the SCE. This highlights the effects of the tri-culture-mediated environment on the cell behavior, and illustrates the efficacy of the tri-culture system developed herein to provide a reliable platform for studying the effects of the paracrine interactions between multiple population of cells on their behavior during a heterogenous culture.

In this study, the most suitable growth medium that would sustain the proliferation of the three different cell types, SFs, STFs as well as OBs in a TCE was optimized. However, this would not have been appropriately accomplished without a suitable tri-culture system that enables studying the three different cells behaviors when grown in different mediums and medium compositions. It is very well known that cell growth can strongly be influenced by the surrounding external environment [1]. For example, cells cultured in a co-culture environment tend to behave differently than when they are cultured in a single culture environment [1]. In a single culture environment, cells tend to normally proliferate if they are provided with the appropriate growth medium. On the other hand, cells cultured with different cellular populations tend to behave differently due to the cell-cell interactions initiated in the co-culture environment, thus, resulting in either an increase or decrease in cell proliferation [1]. Yet there is increasing evidence that the choice of growth media can contribute to the increase or decrease in cell proliferation in the co-culture environment [1]. Therefore, an early optimization of the most suitable growth medium is essential to ensure sustaining the best level of viability and cell proliferation in the co-culture environment.

Figure 4:
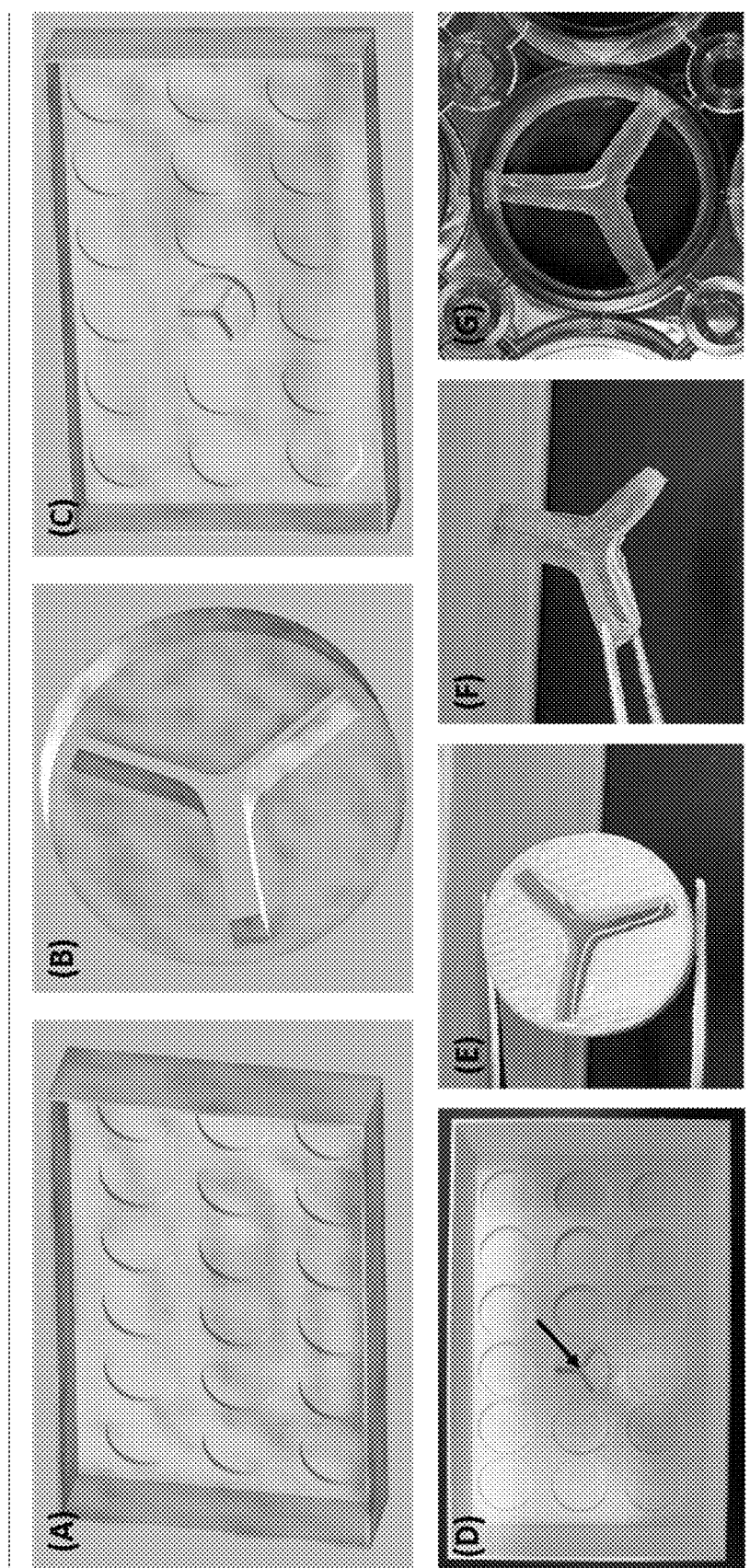
FIG. 4 show 3-D graphical and light images demonstrating the various steps involved in the development of the tri-culture system. (A) A 3-D view showing the plate, and (B) the disc that was used to fabricate the PDMS inserts. (C) The plate served as a platform that housed the disc in the provided holes to prevent the PDMS from leaking from the sides of the disc during the pouring process of the elastomer into the mold. (D) The plate and the disc were 3-D printed, and the disc was inserted into the provided holes within the plate, filled with PDMS elastomer and incubated at 37° C. for 24 hours to allow the PDMS to completely cure. (E) After they cured, (F) the PDMS inserts were removed from the mold and (G) placed inside of a 24-well plate. Placing the PDMS inserts into the well separated the well into three different chambers with symmetrical volumes in which each chamber could be used to culture a different cell population. Black arrow indicates the cavity within the disc in which the PDMS elastomer was poured to form the three-points stars shaped PDMS insert.

In this study, to determine the best suitable medium, a tri-culture model has been developed by conducting very simple procedures that consisted of designing and three-dimensionally printing of a mold that was further used to fabricate PDMS inserts that were used for the establishment of the tri-culture system. Three-dimensional (3-D) printing has emerged as a unique technology that can be employed by disparate fields to fulfil several different needs [2]. This technology is utilized to produce a variety of complex and functional structures with complex geometries using less material than the traditional manufacturing methods in a timely manner. 3D printing applications cover various sectors from education to industry and more recently in tissue engineering for the production of biomimetic scaffolds with precise geometry [2]. In this study, 3-D printing technology was employed to produce a mold that could be further utilized to fabricate PDMS inserts for the establishment of a tri-culture model. However, the mold was successfully designed, and 3-D printed as shown in (FIG. 4D). PDMS is an elastomer which through very simple molding procedure can be shaped into a wide variety of different structures depending on the application's needs [3]. It is transparent, and biocompatible, which explains the strong interest of the scientific community in using this material to fabricate microfluidic devices for cell biological studies as well as to fabricate inserts, boundaries or monolayers for co-culturing studies [3].

The mold consists of two different parts, a disc, and a plate (FIG. 4A-D). The plate, however, served as a platform that housed the disc in the provided holes to prevent the PDMS from leaking from the sides of the disc during the pouring process of the elastomer into the mold. When the PDMS was poured into the mold, no leakage was observed indicating that the disc is well fitted into the holes. After pouring the PDMS into the mold, it was incubated at 37 C for 24 h for the PDMS to cure in order to allow for the formation of the PDMS inserts. PDMS elastomer has the ability to cure at various temperatures ranging from 25 C to 150 C. However, the curing time largely depends on the incubation temperature, where the higher the temperature, the faster it cures. For example, PDMS elastomers incubated at 150 C take up to 10 minutes to cure, while elastomers incubated at 37 C can take up to 24 h to completely cure. Due to the fact that the mold was printed from a plastic material, we had to incubate it at 37 C to prevent the mold from melting. After they cured, the PDMS inserts were removed from the mold and placed inside of the well of the 24-well plate, and they perfectly fitted the well, indicating that the dimensions used in the design were accurate. When designing the mold, dimensions were carefully taken into considerations to ensure the perfect fit of the PDMS inserts into the wells of the 24-well plate.

By placing the PDMS inserts to the wells, the wells were separated into three different chambers, in which each chamber could be used to culture a different cell population. During the design process, the height of the disc (5 mm) had to be quarter the total height of the well of the 24-well plate (20 mm), and that is in order to facilitate the medium exchange between the three different cell types when establishing the tri-culture after placing the PDMS inserts into the wells.

One of the advantages of inserts composed of PDMS is the stickiness observed on its surface after it cures, this property, in particular, supported the integration of the PDMS inserts into the wall and the bottom surface of the TCP when they were placed inside of the wells of the 24-well plate [3]. Since the PDMS inserts are mobile and not physically fixed into the wells of the 24-well plate, we needed to investigate two important factors that had to be met in order to mark the success of the tri-culture system, (1) when culturing cells into the different chambers, cells have to stay and only proliferate within the chamber they are seeded into and not migrate to the other neighboring chambers, and (2) when adding different liquids into the different chambers, they have to remain held within the chamber they are added into and not penetrate to the other chambers. This second point, however, is very important in cases where different reagents such as MTS, Picogreen, immunofluorescent dyes etc. need to be added into the different chambers for running assays to study the behavior of the single cell population in the tri-culture environment.

Figure 5:
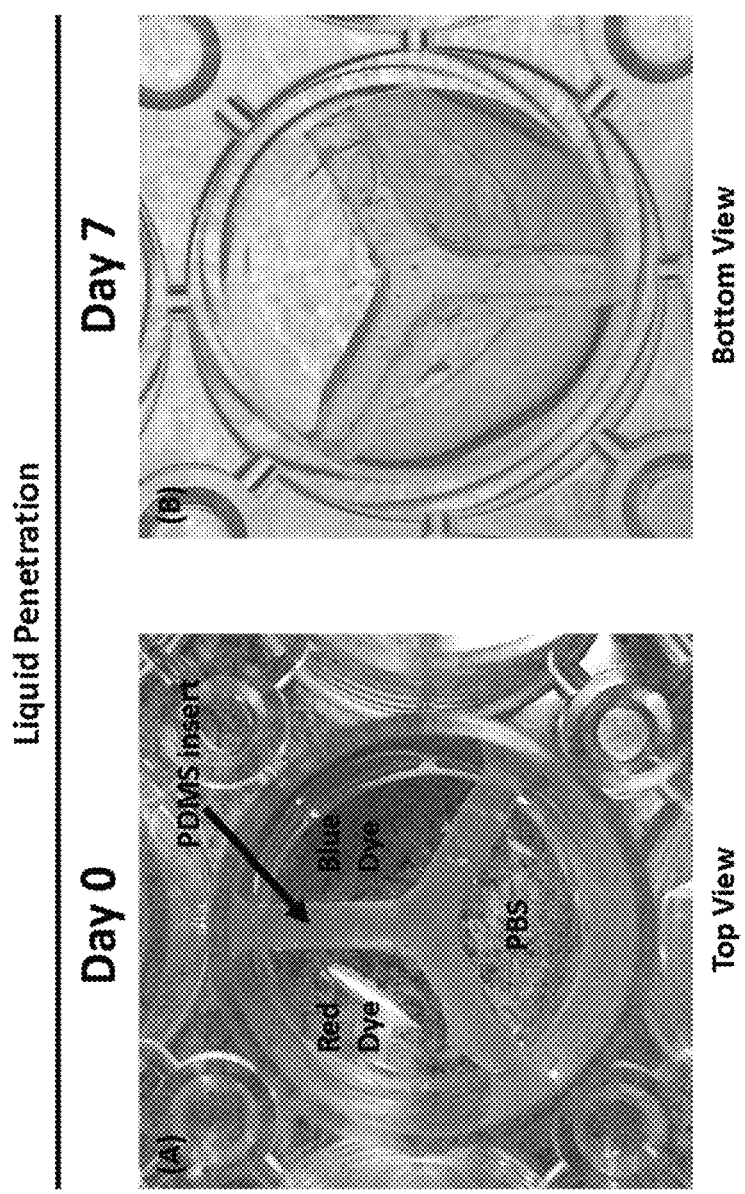
FIG. 5 shows liquid penetration validation of the tri-culture system. To validate the functionality of the tri-culture system, (A) PDMS inserts were inserted into the 24-well plate and the generated chambers were filled with different colored dyes, red, blue and transparent (PBS), and incubated at 37° C. for 7 days on a rotatory rocker. (B) 7 days post-incubation, all dyes were well contained within the chambers they were initially added in and no liquid penetration to the different chambers was observed indicating that the PDMS insert provided a physical barrier between the different chambers.

To examine the liquids penetration, different water-based dyes were added to different chambers after placing the PDMS inserts into the wells of the 24-well plate in which, a red dye was placed in the first chamber, a blue dye was placed in the other chamber, and PBS was placed in the next third chamber, and the liquid penetration was examined after 3 and 7 days of incubation at 37° C. (FIG. 5).

Figure 6:
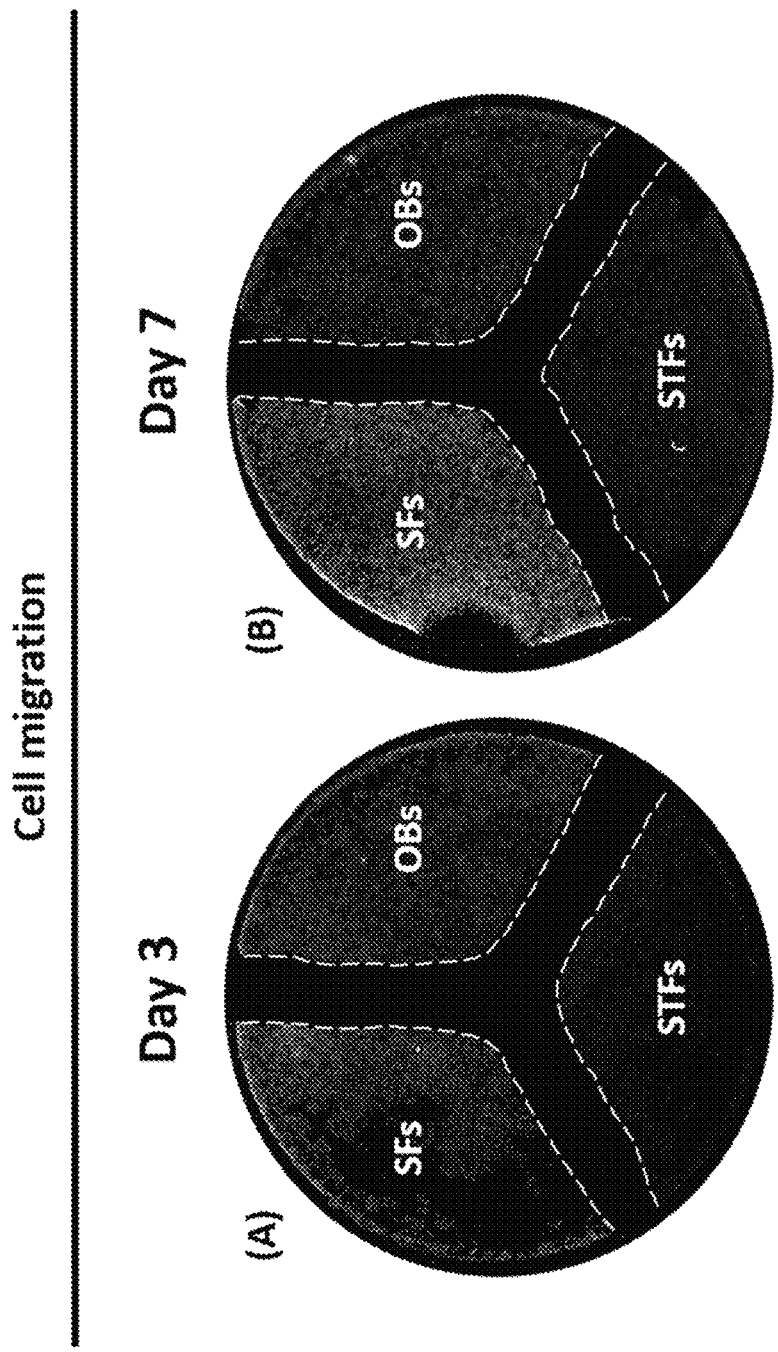
FIG. 6 shows cell migration validation of the tri-culture system. To further validate the functionality of the tri-culture system, PDMS inserts were inserted into the 24-well plate and the generated chambers were seeded with fluorescently labeled SFs, STFs and OBs and incubated at 37° C. for (A) 3 and (B) 7 days. All three cell types were well maintained in their respective chambers and no cellular migration to other chambers was observed at all time points, which further indicates the physical separation provided due to the insertion of the PDMS insert, which acted as a physical barrier between the different cell phenotypes.

No liquid penetration was observed at the two-time points indicating that the PDMS inserts are well fitted into the wells and that they are acting as real physical barriers between the three different chambers. Water molecules are very small, 0.27 nm in size, however, if these very small water molecules could not penetrate from the sides nor underneath the PDMS inserts, cells which are ~10 μm in diameter, should not migrate at all. Although this fact was stated, we still needed to examine the cell migration between the chambers. To do so, the different cell types were fluorescently labeled each with a different colored dye and then seeded in the three chambers and cultured for 3 and 7 days and the cell migration was observed after every time point under a an inverted fluorescence microscope. No evidence for cellular migration between the chambers was seen after the removal of the PDMS inserts from the wells in the two different time points (FIG. 6).

The tri-culture system was further used in order to examine the most suitable growth medium that would best sustain the proliferation of the three different cell types both in the SCE and TCE. To do so, the different cells were each seeded in a different chamber and assayed for proliferation after 3 and 7 days post culture. Using our synthetic tri-culture system, we were able to study the proliferative abilities of the three different cell types cultured alone or in a TCE by exposing them to different mediums and medium compositions. Based on our findings, we could prove the functionality of our tri-culture system and its ability to serve as a valuable system for studying the behavior of the single cell population in a tri-culture environment. Our tri-culture system has emerged to be unique, simple and functional

REFERENCES FOR ABOVE EXAMPLE

1. Sidney L E, Branch M J, Dua H S, Hopkinson A, Effect of culture medium on propagation and phenotype of corneal stroma-derived stem cells. Cytotherapy. 2015 December; 17(12):1706-22. doi: 10.1016/j.jcyt.2015.08.003. E pub 2015 Oct. 9.
2. Gu, Bon Kang et al. "3-Dimensional Bioprinting for Tissue Engineering Applications." *Biomaterials Research* 20 (2016): 12. PMC. Web. 1 Nov. 2017.
3. Velve-Casquillas, Guilhem et al. "Microfluidic Tools for Cell Biological Research." *Nano today* 5.1 (2010): 28-47. PMC. Web. 1 Nov. 2017.

Robust Phenotypic Maintenance of Limb Cells During Heterogeneous Culture in a Physiologically Relevant Polymeric-Based Constructed Graft System After optimizing the growth medium as described in example 1A, this optimized growth medium was used to support the growth of SFs, STFs and OBs while seeded in a constructed graft system (CGS) to evaluate the efficacy of the CGS in regulating the cell behavior during tri-culture as described below.

The CGS is a scaffolding system that is composed of three regions, with each region engineered to mimic the physiological microstructure of SFs (region A), STFs (region B), and OBs (region C). It was found that providing biomimetic structural cues relevant to each cell phenotype plays a crucial role in regulating the behavior of the distinct cell populations during a heterogeneous culture, as the cells were able to restore their normal physiological functions such as a normal proliferation.

Optimizing the optimal growth medium for the three different cell phenotypes during the tri-culture as described in example A1 was essential to ensure that when the cells are seeded in their respective regions within the CGS, any changes in cellular behavior are due to the effects of the paracrine interactions and/or the structural cues provided within the CGS and not due to the type of culture medium, since the growth of cells could be affected depending on the type of medium used in culture. Here, predetermining the optimal growth medium was done using the disclosed system herein as described in example 1A.

In this study, we developed a constructed graft system (CGS) that spatially modeled the 3D microenvironment of skin, soft tissue and bone. The CGS is composed of three combined regions, each exhibiting a different microstructure and contains a different growth factor. Region A of the CGS modeled the fibrous microstructure of the skin tissue and contained recombinant human platelet-derived growth factor (rhPDGF-BB), region B modeled the fibrous microstructure of soft tissues and contained recombinant human insulin-like growth factor-I (rhIGF-I), and region C modeled the interconnected and highly porous microstructure of the bone tissue and contained recombinant human bone morphogenetic protein-2 (rhBMP-2) (FIG. 8A). Both rhPDGF-BB and rhIGF-I were physically incorporated into their respective regions, while rhBMP-2 was covalently bonded to region C. SFs, STFs, and OBs were isolated from rats and seeded on their respective regions (FIG. 8B) followed by physically assembling the different regions into a 3D multi-layered configuration (FIG. 8C,D). Combining the different regions into this 3D configuration resulted in the production of a single construct with spatial heterogeneity in structure, growth factor type, and cell phenotype, mimicking the structural, cellular and chemical heterogeneity found in the native in vivo milieu. We first investigated the potential of biomimetic structural cues provided within the CGS to maintain the heterogeneity of the different cells in a region-specific manner during a heterogeneous culture. We next evaluated the feasibility of the CGS to act as a bioactive milieu by investigating its ability to contain and present different growth factors simultaneously to enhance the different cells' physiological functions in a region-specific manner while maintaining distinct cellular regions. Our data suggest that the biomimetic structural cues provided within the CGS and the proper presentation of growth factors played a crucial role in ensuring heterogeneity maintenance of distinct cell populations during a heterogeneous culture. The presented CGS herein provides a reliable platform for investigating different cells responses to heterogeneous culture in a physiologically relevant microenvironment. In addition, the model provides a unique platform for evaluating the feasibility and efficacy of different approaches for simultaneously delivering multiple growth factors or molecules from a single construct to achieve enhanced cell response while maintaining cellular heterogeneity during a heterogenous culture.

Materials and Methods:

Fabrication of the Three Different Regions within the CGS.

Both regions A and B were fabricated by coaxial electrospinning. To do so, 16% (w/v) PLGA (85:15) (DURECT, Birmingham, Ala., USA) (Mw≈152 kDa) in 1,1,1,3,3,3-Hexafluoro-2-propanol (HFIP, Sigma-Aldrich, MO, USA) (shell solution), and 4% (w/v) type A gelatin (MP Biomedical, OH, USA) in HFIP alone or containing either rhPDGF-BB or rhIGF-I (Fisher Scientific, NH, USA) at a final concentration of 27 µg/mL (core-shell solution) were loaded into two separate 10 mL syringes and connected to a coaxial apparatus containing two concentric needles with different diameters, a 16 G (ID=1.6 mm) outer needle and a 22 G (ID=0.7 mm) inner needle. Each syringe was placed on a different electrospinning apparatus (NE 300 SYRINGE pumps, USA) and electrospun with varying flow rates, 1.5 mL/h for the shell solution and 0.75 mL/h for the core-shell solution at an applied voltage of 10 kV with the tip of the coaxial apparatus placed 10 cm away from the collector. The formed coaxial nanofibers were peeled from the collector, cut into 10 mm×20 mm small scaffolds, and stored under a vacuumed desiccator for 24 hours to ensure complete evaporation of solvent before use.

Region C was fabricated by heat sintering PLGA microspheres. Briefly, 12.5% (w/v) PLGA (85:15) in dichloromethane (Fisher Scientific) was poured into a 1% polyvinyl alcohol (Sigma-Aldrich) solution and was left to stir at 300 RPM overnight to form PLGA microspheres. Microspheres in the range of 300-600 µm were collected and packed into a cylindrical 10 mm×10 mm stainless-steel mold and heat sintered at 90° C. for 90 minutes to construct region C. For rhBMP-2 (Fisher Scientific) incorporation into region C, 3% (w/v) type A gelatin in PBS (Gibco, NY, USA), and 10% (w/v) mTG (Ajinomoto, Japan) in PBS were sterilized through 0.22 µm filter and subsequently mixed at a ratio of 10:1 and stirred at 37° C. for 5 minutes to initiate gelatin gelation. Semi-gelled gelatin-mTG solution was mixed with rhBMP-2 at a final concentration of 10 µg/mL, and 100 µL of the produced mixture was injected into region C using an insulin syringe until the pore volume of the construct was filled, followed by incubation at 37° C. for 1 hour to allow for a complete gelation of gelatin. For region C fabrication without rhBMP-2, gelatin-mTG solution was injected alone.

Scanning Electron Microscopy (SEM).

All regions were morphologically evaluated under scanning electron microscopy post-fabrication using FEI Nova NanoSEM 450 (FEI Ltd., Tokyo, Japan) at a working distance of 5 mm and an acceleration voltage of 18 kV. Specimens were mounted on 15 mm stubs and were gold sputter-coated using (Polaron E5100) for 3 minutes to eliminate surface charging. Finally, the coated samples were loaded into the SEM and high magnification images of each region were taken.

Particle Size Distribution and Porosity Analysis.

Four to six different images from every sample/region (n=4 per region) were obtained and analyzed for particle size distribution using Image J software (version 1.4 g, National Institute of Health, USA). To measure the porosity of every region (n=4 per region), the following equation was used[1]:

$$\text{Region apparent density}(g/cm^3) = \frac{\text{region Mass}(g)}{\text{region Volume}(cm3)}$$

$$\text{Region porosity} = \left(1 - \frac{\text{region apparent density}(g/cm3)}{\text{bulk density of } PLGA(g/cm3)}\right) \times 100\%$$

Transmission Electron Microscopy (TEM).

TEM analysis was conducted to confirm the coaxial structure of the nanofibers in both regions A and B. Observations were prepared by directly depositing the spun fibers onto copper grids of a 300 mesh. The samples for TEM images were analyzed using (FEI Tecnai 12 G2 Spirit BioTWIN) and all images were recorded in a GATAN ESW 500 camera.

In Vitro Cumulative Release of Growth Factors from Different Regions.

The cumulative release of different growth factors incorporated into the different regions was measured for 14 days. Briefly, regions A, B, and C (n=5 per each region) were placed in 5 mL glass vials filled with 2 mL of PBS and incubated at 37° C. under continuous agitation. At predetermined time points (0, 24, 36, 48, 60, 72 hours and then every day for 11 days), 125 µl from every sample was collected and replaced with 125 µl of fresh PBS. Collected samples were stored at −20° C. for later analysis. The cumulative release patterns of the different growth factors incorporated into the different regions were analyzed using the corresponding ELISA-kit (All from Fisher Scientific) to each protein following the manufacturer's instructions. The initial protein content in both regions A and B was determined by a base-surfactant method[2]. Briefly, scaffolds of each region (n=5) were subjected to hydrolysis in 0.1N Sodium hydroxide (NaOH), 5M Urea, 0.08% sodium dodecyl sulfate (SDS) in 50 mM Tris extraction medium at 37° C. for 3 hours. After neutralization with 0.1N Hydrochloric acid (HCL) and centrifugation, the protein concentration in the supernatant was measured using the corresponding ELISA-kits. For extracting the retained rhBMP-2 from gelatin-mTG in region C the same samples were incubated in 5 mL of 0.1% type collagenase I (ThermoFisher, MA, USA) solution in PBS at 37° C. until gelatin-mTG was digested, followed by measuring the protein content in the supernatant using corresponding ELISA-kits. For evaluating the bioactivity of the retained rhBMP-2 in gelatin-mTG in region C, MC3T3 cells (ATCC, VA, USA) were seeded on region C at a density of $1 \times 10^5$ cells/sample and maintained at 37° C., and 5% $CO_2$ in 1 mL of MEM-α (1×) supplemented with 10% fetal bovine serum (FBS) and 1% Penicillin-Streptomycin 10,000 U/mL (P/S) (Gibco). Region C-free of rhBMP-2 and region C-free of rhBMP-2 with 1 µg/mL of rhBMP-2 added to the culture medium served as negative and positive controls, respectively (n=3 per every sample). At 7 and 14 days, ALP activity was measured using a BCA total protein kit (ThermoFisher) following the manufacturer's instructions. Briefly, cells in region C were lysed by incubation in 1 mL of 0.1% Triton X-100 (Bio-Rad, CA, USA) through a freeze-thaw cycle and centrifugation. The cell lysate from every sample was used for the assay. ALP values were normalized to total protein values.

Primary Cell Isolation and Culture.

All animal experiments were approved by the Institutional Animal Care and Use Committee (IACUC) at the University of Connecticut Health Center, CT, USA. All methods were performed in accordance with the relevant guidelines and regulations. Lewis rats (male, 6-8 weeks old) (Charles River Laboratories, MA, USA) were used for all primary cell isolations following previously established protocols with some modifications[3-5]. SFs were maintained in culture in MEM supplemented with 10% FBS and 1% P/S. STFs were maintained in DMEM-F12 supplemented with 10% FBS, 1% P/S, and OBs were maintained in MEM-α (1×) supplemented with 10% FBS and 1% P/S (all from Gibco). All primary cells were used at the second passage for further experiments.

CGS Development and In Vitro Evaluations of Region-Specific Heterogeneity Maintenance.

The CGS was cultured in three different conditions; (1) CGS (cells only), (2) CGS+GFs (cells and growth factors directly supplemented in medium) and (3) CGS-GFs (cells and growth factors incorporated into their designated regions). Developing the CGS was achieved through multiple steps. First, all regions were sterilized prior to cell seeding. Regions A and B containing growth factors or free of growth factors were sterilized by direct exposure to ultraviolet (UV) light for 30 minutes per side. Region C was sterilized by immersion in 70% ethanol for 30 minutes, followed by immersion in PBS for 30 minutes and then exposed to UV light for 30 minutes per side. Gelatin-mTG solution containing rhBMP-2 or free of rhBMP-2 was incorporated into region C after sterilization. Regions A, B, and C were placed separately in low-binding 24-well plates (n=3/region/condition) and seeded with SFs, STFs, and OBs, respectively, at a density of $1 \times 10^5$ cells/region. Cells were allowed to partially attach for 1.5 hours at 37° C. Next, 1 mL of MEM-α (1×) supplemented with 10% FBS and 1% P/S alone or premixed with the corresponding growth factors at a concentration of 1 µg/mL was added to each region and maintained in an incubator at 37° C., and 5% $CO_2$ for 2 days to allow the cells to completely adhere to their respective regions. At day 2, all regions were harvested and brought together to construct the CGS in which region B was wrapped around region C, followed by wrapping region A around both regions B and C. The regions were then tied using 5-0 vicryl sutures (Ethicon. Inc, NJ, USA) to keep them in place and placed in fresh low-binding 24-well plates. One mL of the medium was added to both conditions 1 and 3 or premixed (condition 2) with the three different growth factors at a concentration of 1 µg/mL per growth factor and further incubated. Three and 7 days post-CGS development, the CGS was harvested, regions were separated, washed twice with PBS and assayed for cell viability, proliferation, migration, and phenotypic maintenance.

For cell viability evaluations, live/dead assay/cytotoxicity kit (Invitrogen, CA, USA) was used following the manufacturer's instructions. Briefly, every region was incubated in 1 mL of the assay solution (2 µL/mL EthD-1, and 0.5 µL/mL calcein-AM in PBS) for 1 hour at room temperature (RT) in the dark. Next, regions were washed twice with PBS and 4-6 random images per each sample were taken.

For proliferation evaluations, an MTS assay (MTS, Promega Inc, WI, USA) was performed following the manufacturer's instructions. Every region was incubated in 1 mL of a cocktail solution of the MTS reagent premixed with the medium at a ratio of (1:5) for 3 hours at 37° C. in the dark. Next, 100 uL from each sample was collected and transferred to a 96-well plate and the absorbance was measured at 490 nm with a spectrophotometric (TECAN, Crailsheim, Germany).

For migration evaluations, the cells' cytoskeletal protein, actin, was stained by rhodamine-phalloidin staining. Regions were fixed in 4% paraformaldehyde (Sigma-Aldrich) in PBS for 20 minutes, permeabilized with 0.1% Triton X-100 for 10 minutes, and blocked with 1% bovine serum albumin (BSA, Sigma-Aldrich) for 30 minutes. Regions were then stained with F-actin Alexa Fluor 594-conjugated (1:50) (Invitrogen) for 60 minutes in the dark, followed by nuclei staining with 4', 6-Diamidino-2-Phenylindole, Dihydrochloride (DAPI, Invitrogen) at a concentration of 1:3000 for 10 minutes. Regions were then washed twice with PBS and 4-6 random images per sample were taken. Staining was performed at RT.

For phenotypic maintenance evaluations, immunofluorescent staining for vimentin (VIM), scleraxis (SCXA) and alkaline phosphatase (ALP) was performed. Regions were fixed with 4% paraformaldehyde in PBS for 20 minutes, permeabilized with 0.1% Triton X-100 for 10 minutes and blocked with 10% goat serum (Gibco) in PBS for 1 hour. Region A was then incubated with anti-vimentin (ab92547, 1:500 Abcam, Cambridge, UK) or anti-ALP (ab218574, 1:100, Abcam), region B was incubated with anti-SCXA (ab58655, 1:1000, Abcam) or anti-ALP, and region C was incubated with anti-ALP in the same blocking buffer for 2 hours. Following, regions were washed twice with PBS and incubated with the secondary antibodies goat anti-rabbit Alexa Fluor 488 (ab150077, 1:500, Abcam) or goat anti-rabbit Alexa Fluor 594 (ab150080, 1:500, Abcam) for 2 hours in the dark, followed by washing twice with PBS and incubation in DAPI (1:3000) for 10 minutes. Regions were then washed twice with PBS and 4-6 random images per each sample were taken. Staining was performed at RT. All samples for cell viability, migration, and phenotypic maintenance evaluations were visualized using an inverted fluorescence microscope (Zeiss LSM 880, Oberkochen, Germany) using Zen Software. Protein expression in all images was quantified by measuring the mean intensity values using ImageJ software (n=3 and 4-6 random fields per sample).

In Vitro Cumulative Release of Different Growth Factors Incorporated into the CGS During Culture.

The cumulative release of the different growth factors incorporated into the CGS was measured for 7 days during culture. Briefly, the CGS was sterilized, populated with cells, developed, and cultured as described previously (n=5). At predetermined time points (0, 12, and 24 hours, and then every day for 6 days), 75 µL from every sample was collected and replaced with 75 µL of fresh medium. Collected samples were stored at −20° C. for later analyses. The cumulative release of the different growth factors was analyzed using the corresponding ELISA-kit to each protein following the manufacturer's instructions. Routine medium change was not done as to maintain constant protein levels during the release study.

Statistical Analysis.

Data are presented as mean standard deviation (SD). All statistical analyses were performed using the statistical software Prism GraphPad version 8 (GraphPad, San Diego, Calif.). One or where appropriate two-ways analysis of variance (ANOVA), Tukey post hoc testing and Student 1-tests were applied to mean comparisons. The difference between experimental groups was considered statistically significant at a P value of less than 0.05.

Results:

Regions with Structural Heterogeneity.

The three different regions of the CGS were each fabricated using a different process to achieve regions with biomimetic structures relevant to each cell phenotype. Specifically, regions A and B were produced by electrospinning of poly (lactic-co-glycolic acid) (PLGA), and region C was produced by heat sintering of PLGA microspheres above its glass transition at 90° C. for 90 minutes[6]. PLGA was selected as the core material for the fabrication of the three different regions due to its biocompatibility and ability to be processed into different structures[7]. In addition, fabricating the three different regions using the same material was essential for our investigation to ensure that any changes in cellular behaviors observed during the study are due to the effects of the heterogeneous culture and/or the structural cues provided within the CGS and not due to variation in the type of material used.

Figure 9:
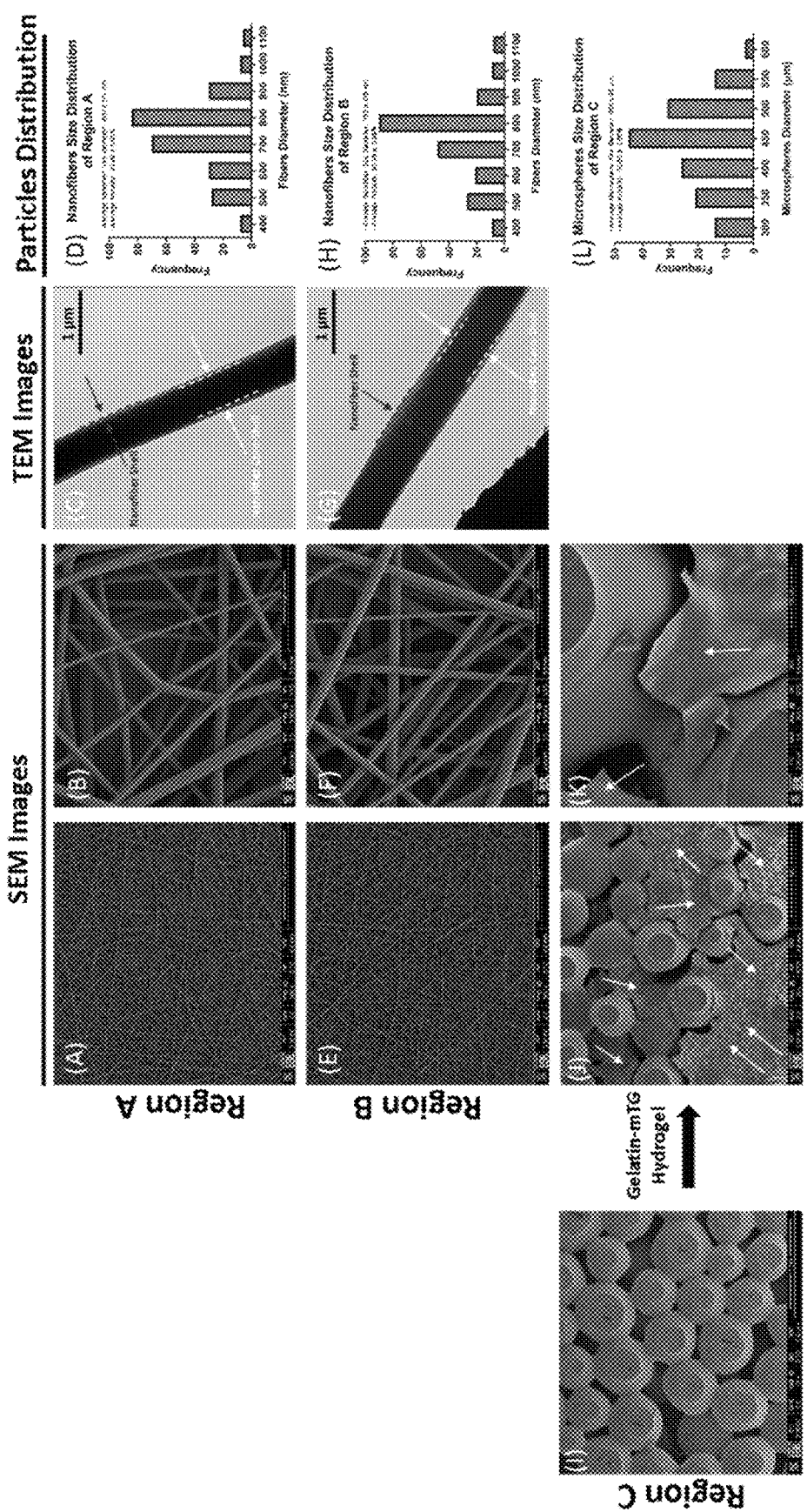
FIG. 9 shows morphology and properties of the different CGS regions. SEM images of regions A, B and C post-fabrication demonstrating the biomimetic structures to the corresponding native tissues as well as high porosities. (A, E) Overall morphology of the electrospun nanofibers for both regions A and B (scale bar 100 μm). (B, F) Higher magnification images showing the morphology of individual nanofibers and the pore spaces between them. Smooth nanofiber surface can be observed and a biomimetic fibrous structure similar to skin and soft tissues (scale bar 5 pam). (C, G) TEM images of PLGA-Gelatin Coaxial nanofibers with a clear core-shell structure, where gelatin is contained in the core and covered with a PLGA shell. (D, H) The size distribution of electrospun nanofibers in both regions A and B ranged between (400 nm-1100 nm), mimicking the size range of collagen fibril found in the native skin and soft tissues. Both regions A and B exhibited high porosity with an average of 97.68±0.65% and 97.96±0.98%, respectively. (I) Overall morphology of the sintered microspheres in region C before and (J) after the incorporation of gelatin-mTG hydrogel into the pore spaces of the construct (scale bar 500 µm). (K) Higher magnification image showing the interconnectivity between microspheres and gelatin-mTG hydrogel occupying the pore spaces (scale bar 100 µm). (L) PLGA microspheres size distribution in region C ranged between (300 µm-600 µm), resulting in an optimal porosity for bone tissue regeneration (41.64±1.65%). Dotted lines represent the nanofiber shell, white dotted lines represent the core-shell of the nanofiber, and Gray arrows represents gelatin-mTG hydrogel.

The gross appearance of all regions was examined using scanning electron microscopy (SEM) (FIG. 9). SEM images of both regions A and B show that the electrospinning process resulted in the production of a fibrous network that mimicked the fibrous microenvironment of skin and soft tissues (FIG. 9A,B,E,F). These synthetic nanofibrous structures have previously been shown to act as suitable platforms for the attachment and growth of SFs and STFs as well as the regeneration of their respective tissues[8-10]. Therefore, utilizing such structures in both regions A and B is feasible for addressing the current study's questions.

Nanofibers in both regions A and B were obtained by coaxial electrospinning. This resulted in nanofibers with a core-shell structure as confirmed by the transmission electron microscopy (TEM) images (FIG. 9C,G), in which the core contains the growth factor solution and is covered by a PLGA shell. In this study coaxial electrospinning was selected over the conventional blend electrospinning (growth factors blended with the polymer solution during electrospinning) for the production of both regions A and B for its ability to (1) provide homogenous distribution of the incorporated growth factor throughout the fibers, (2) protect the bioactivity of the incorporated growth factors from the harmful effects of the electrical currents that are normally localized on the outer surface of the nanofiber during the electrospinning process, and most importantly (3) significantly minimize the initial burst release of the incorporated factor, as well as sustain, prolong, and localize its release within a limited domain[2,11,12].

The SEM images of region C show that the heat sintering process of PLGA microspheres resulted in the production of an interconnected microsphere network that mimicked the microstructure and interconnectivity seen at the native bone tissue (FIG. 9I). The capacity of these sintered microsphere-based structures to support OBs growth, as well as bone regeneration has been well demonstrated in previous literature, making them an excellent choice for bone tissue regeneration applications[13-15].

After the fabrication of region C, its pore volume was completely filled with gelatin-microbial transglutaminase (Gelatin-mTG) solution containing rhBMP-2, followed by incubation at 37° C. for 1 hour to allow the gelatin-mTG-rhBMP-2 solution to completely gel within region C. Gelatin is naturally derived from collagen, is biocompatible, and favored by cells[16]. Gelatin-based hydrogels are generally used as carriers for the delivery of biomolecules such as rhBMP-2 due to the ability to control the release profiles of the incorporated factors depending on the crosslinking method[17,18]. Here, gelatin was used as the carrier for rhBMP-2 and was enzymatically crosslinked with mTG since this enzyme can initiate covalent bonding between gelatin and rhBMP-2[19]. Thus, the incorporation of the gelatin-mTG-rhBMP-2 hydrogel into the pore volume resulted in covalently bonded rhBMP-2 within region C. FIG. 9J, K shows an even distribution of the incorporated gelatin-mTG-rhBMP-2 hydrogel within the pore spaces of region C (white arrows) indicating its successful incorporation.

To maintain the viability of the cells within CGS we modulated the porosity in all regions during the fabrication process to allow for sufficient oxygen and nutrient diffusion, as well as metabolic waste removal. This was done based on preliminary optimization studies performed in our laboratory that led to the selection of general electrospinning parameters[20] as well as microsphere size distribution[21] to yield constructs with high porosity throughout. As a result, all regions exhibited high porosity (97.68±0.65%, 97.96±0.98% and 41.64±1.65%, respectively) (FIG. 9D,H,L).

CGS Development and In Vitro Evaluations of Region-Specific Cell Heterogeneity Maintenance.

Figure 8:
FIG. 8 shows a schematic showing the various steps involved in the development of the CGS. (A) Regions A, B and C containing rhPDGF-BB, rh-IGF-I and rh-BMP-2. (B) Each region populated with the relevant cell type and cultured separately in the optimal heterogeneous growth medium for 2 days to allow cells to completely adhere to their respective regions. (C) Two days post-initial culture, regions harvested and assessed for CGS development in which region B is wrapped around region C and both regions B and C are wrapped by region A, followed by suturing the regions. (D) Post-CGS development, the CGS is further cultured for 3 and 7 days. After 3 and 7 days, CGS is harvested, regions are separated and assayed for cell survival, proliferation, migration, and phenotypic maintenance.
Figure 8:
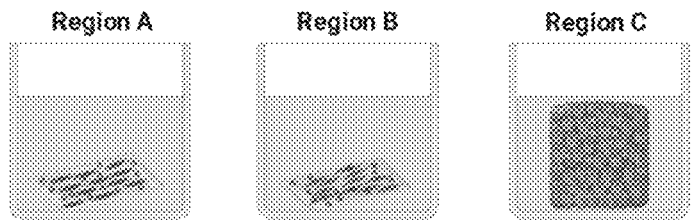
Figure 8:
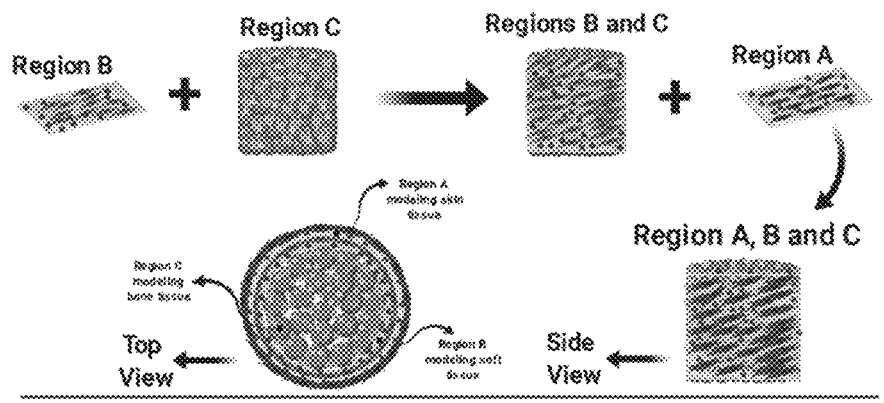
Figure 8:
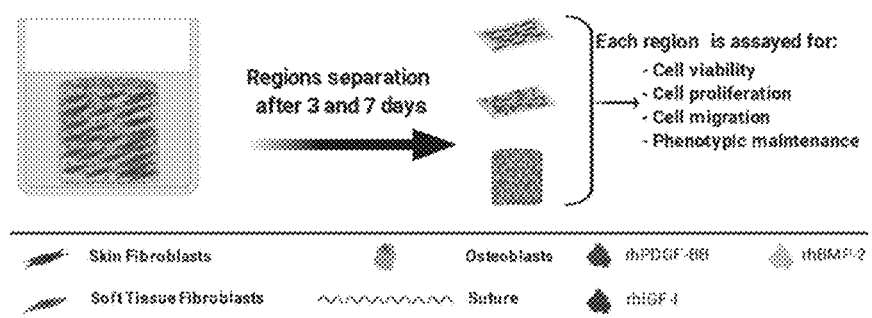
Figure 14:
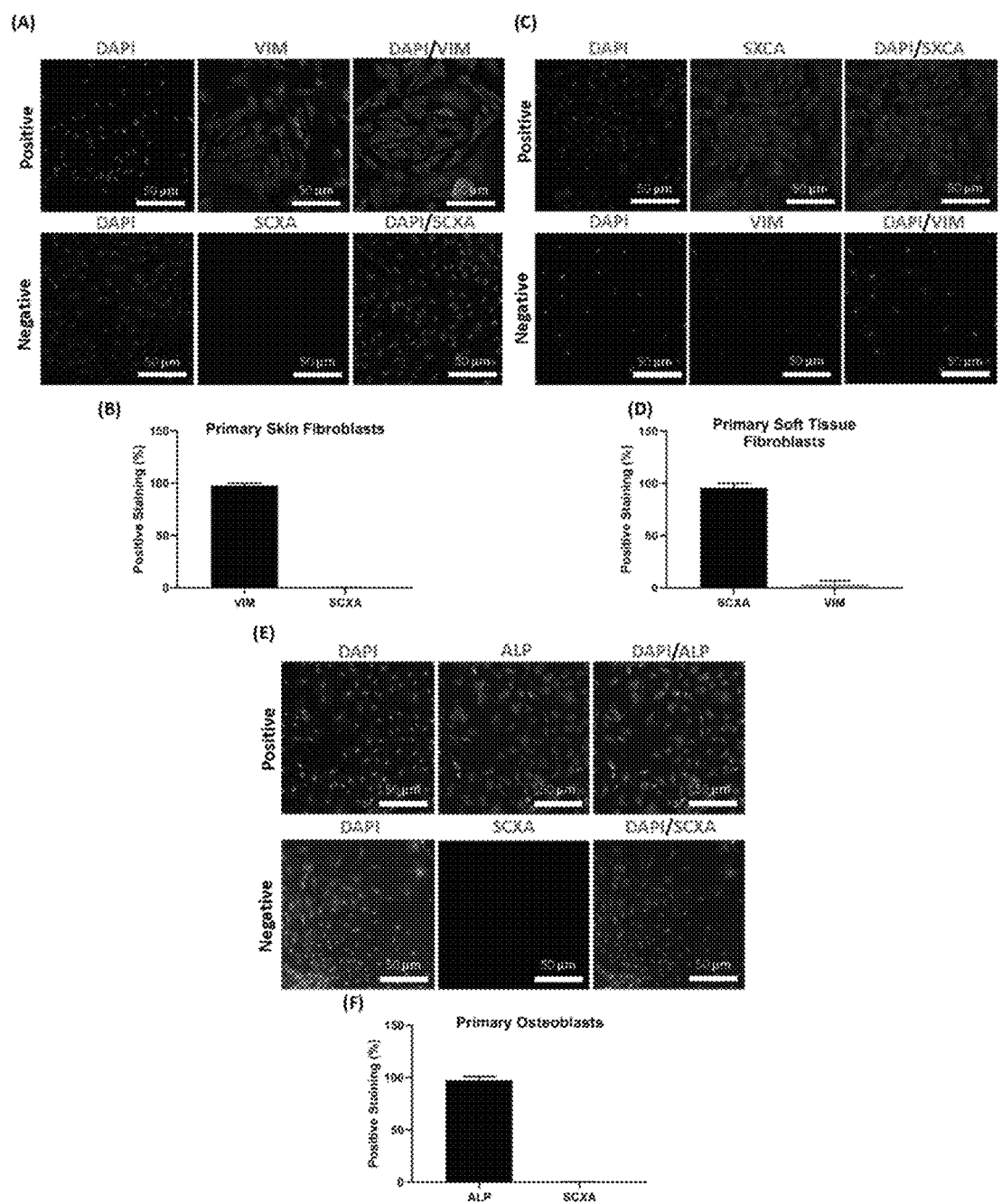
FIG. 14 shows immunofluorescent phenotypic characterization of isolated primary cells and their corresponding positive staining quantifications. (A-F) All isolated cells were positive for their corresponding markers and negative for the controls, indicating the homogeneity in the isolated cellular population. STFs showed a slight expression to the SFs specific marker VIM, indicating that it also can be expressed in STFs but in lower amounts.

Previous reports have shown that in 2D monolayer-based co-culture systems both SFs and STFs undergo trans-differentiation to an osteogenic lineage when co-cultured with OBs due to the robust paracrine effects mediated by OBs[22,23,24]. Therefore, in this study, we sought to investigate whether combining both fibroblastic phenotypes with OBs in a 3D physiologically relevant microenvironment can reveal different cell responses than what has been reported in the 2D monolayer-based cultures and can help regulate their relative physiological functions and phenotypic characteristics during paracrine interactions. We developed a CGS with biomimetic structural cues relevant to each cell phenotype. Developing the CGS was achieved by first seeding the three different cell phenotypes in their respective regions separately and culturing them for 2 days to allow for complete cell adherence. Prior to seeding the isolated primary cells, they were phenotypically characterized by immunofluorescent to confirm their lineages specificity (FIG. 14). Two days post-initial seeding, the multiple regions were harvested and combined by assembling them in a 3D multi-layered configuration (FIG. 8). Combining the multiple regions in this 3D configuration resulted in the production of a single construct with spatial heterogeneity in structure and cell phenotype in a region-specific manner. The rationale for the graft system's design, in terms of lacking the structural continuity between the different regions, is to allow the cells to only interact by paracrine factors while residing in their respective regions within the CGS. Thus, enabling the determination of the role of biomimetic structural cues presented within the CGS to maintain the different cells' heterogeneity during paracrine interactions, and the potential of the CGS to act as a physiologically relevant milieu for studying different cell responses to heterogeneous culture.

Figure 7:
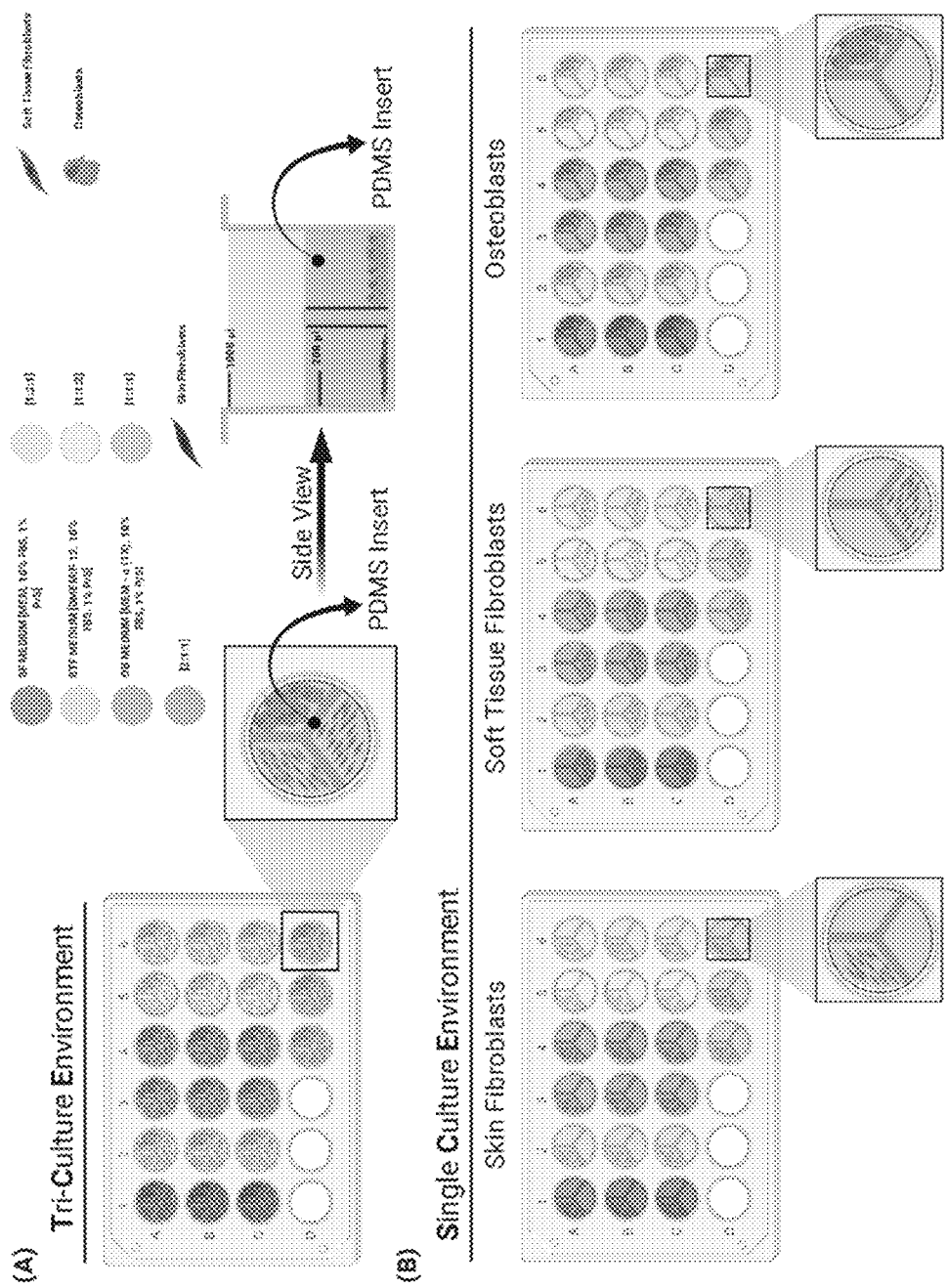
FIG. 7 shows representative schematic demonstrating the experimental setup for the determination of an optimal heterogeneous growth medium for the three different cell types in (A) condition 1: Tri-culture environment (TCE) and (B) condition 2: single culture environment (SCE)
Figure 15:
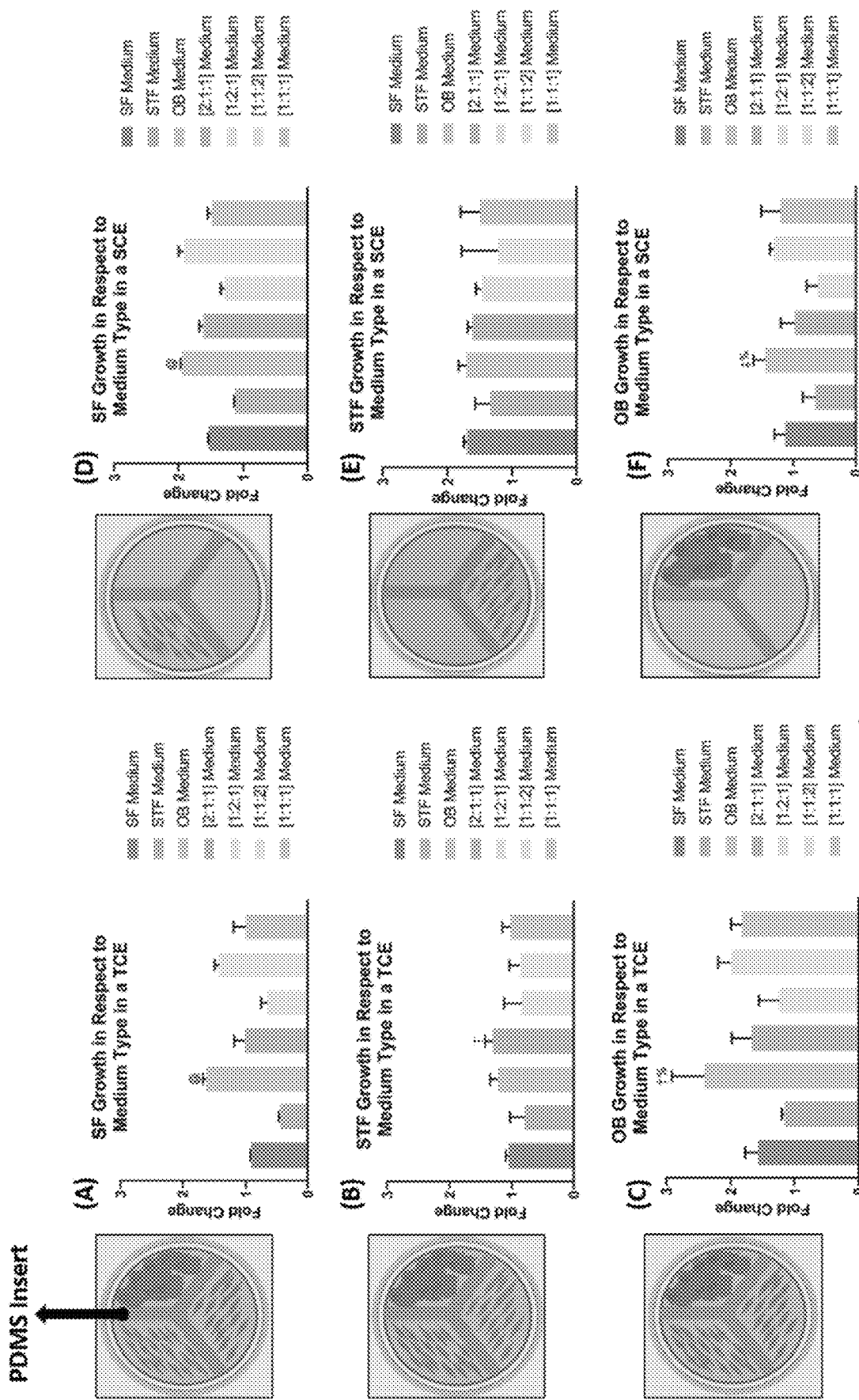
FIG. 15 shows the growth of SFs, STFs and OBs in respect to medium type in a TCE and SCE. (A) The growth of SFs in different types of medium in a TCE; (B) the growth of STFs in different types of medium in a TCE; and (C) the growth of OBs in different types of medium in a TCE. (D) The growth of SFs in different types of medium in a SCE; (E) the growth of STFs in different types of medium in a SCE; and (F) the growth of OBs in different types of medium in a SCE. Results indicate that OBs medium supported the growth of the three different cell types in both conditions, the TCE and SCE, suggesting its suitability as an optimal heterogeneous growth medium for further experiments. Diagrams to the left of the figures are representation of the experimental setup, each were coded with the color of the medium that supported the growth of each cell type.

Post-CGS development, it was further cultured for 3 and 7 days to allow for paracrine interactions to occur. During the 7 days, the CGS was cultured in a predetermined heterogeneous growth medium that was shown to support the growth of the three different cell phenotypes in a tri-culture (FIGS. 7, 15 and Table 1).

Predetermining the optimal heterogeneous growth medium for the three different cell phenotype during the tri-culture was essential to ensure that any changes in cellular behavior was due to the effects of the paracrine interactions and/or the structural cues provided within the CGS and not due to the type of culture medium since the growth of cells could be affected depending on the type of medium used in culture[25].

Predetermining the optimal heterogeneous growth medium was achieved through the utility of a tri-culture system that was developed (FIG. 4) in our laboratory and validated for its functionality (FIGS. 5 and 6). Using this tri-culture system, we were able to determine an optimal growth medium that supported the growth of the three different cell phenotypes.

While this tri-culture system was particularly developed and utilized in this study for determining an optimal growth medium that would support the growth of SFs, STFs, and OBs during heterogenous culture, it can also be used to for the same purpose on other cell phenotypes, or for the purpose of studying the effects of the paracrine interactions between distinct population of cells in a monolayer environment for early-stage research investigations.

At 3 and 7 days, the ability of the CGS to maintain the region-specific heterogeneity during the heterogeneous culture was determined by harvesting the CGS, separating the regions and assaying each region for cell viability, proliferation, migration, and phenotypic maintenance.

Figure 10:
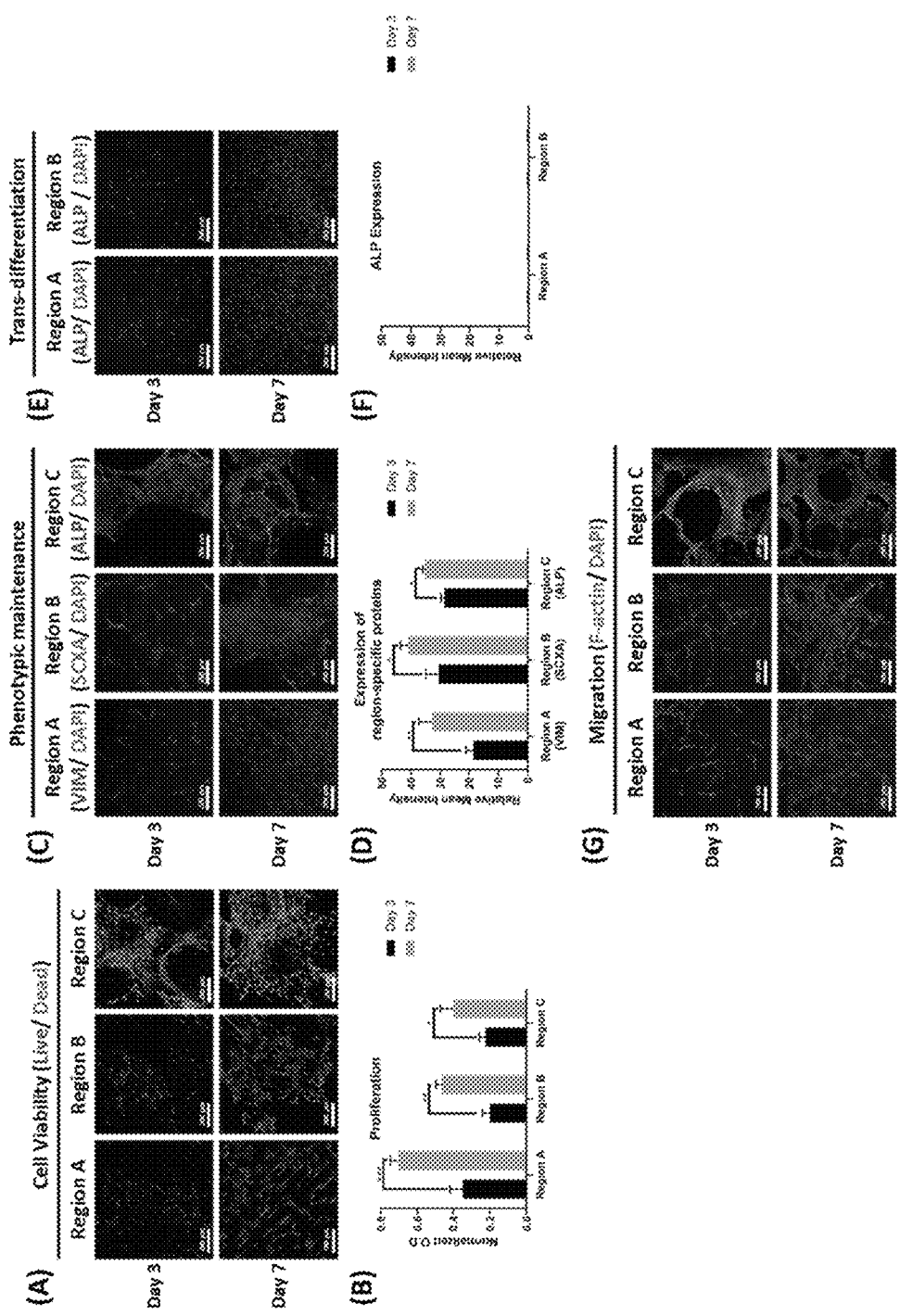
FIG. 10 shows in vitro evaluation of the physiological functions and phenotypic characteristics in each region of the CGS during a heterogeneous culture. (A) Representative live/dead staining images for regions A, B and C at 3 and 7 days. (B) Proliferation of SF, STF and OBs in regions A, B and C, respectively at 3 and 7 days. (C) Immunofluorescent staining of regions A, B and C for VIM, SCXA and ALP at 3 and 7 days, respectively. (D) Quantifications of VIM, SCXA and ALP expression from regions A, B and C at 3 and 7 days, respectively. (E) Immunofluorescent staining of regions A and B for ALP at 3 and 7 days, respectively. (F) Quantifications of ALP expression from regions A and B at 3 and 7 days. (G) Representative F-actin staining images for regions A, B and C at 3 and 7 days.

Our data shows that the biomimetic structural cues provided within the CGS were able to maintain the different cells' physiological functions and phenotypic characteristics during paracrine interactions, as they were able to maintain high viability, proliferation, migration, and phenotypic maintenance abilities at both time points as demonstrated by live/dead assay staining, MTS assay, actin staining, as well as immunofluorescent staining (FIG. 10).

Figure 1:
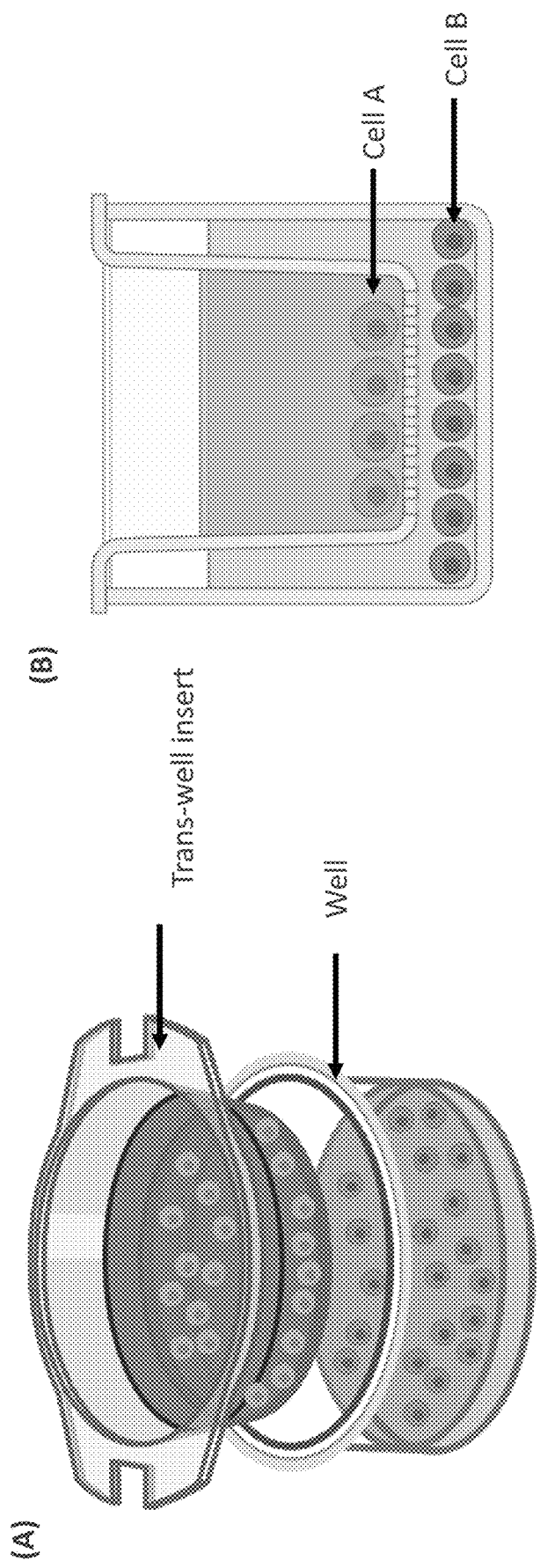
FIG. 1 shows the trans-well of the prior art from the top (A) and from the side (B). This set-up allows for culturing only two population of cells; one to be cultured at the bottom of the well plate and one at the bottom of the trans-well insert.
Figure 2:
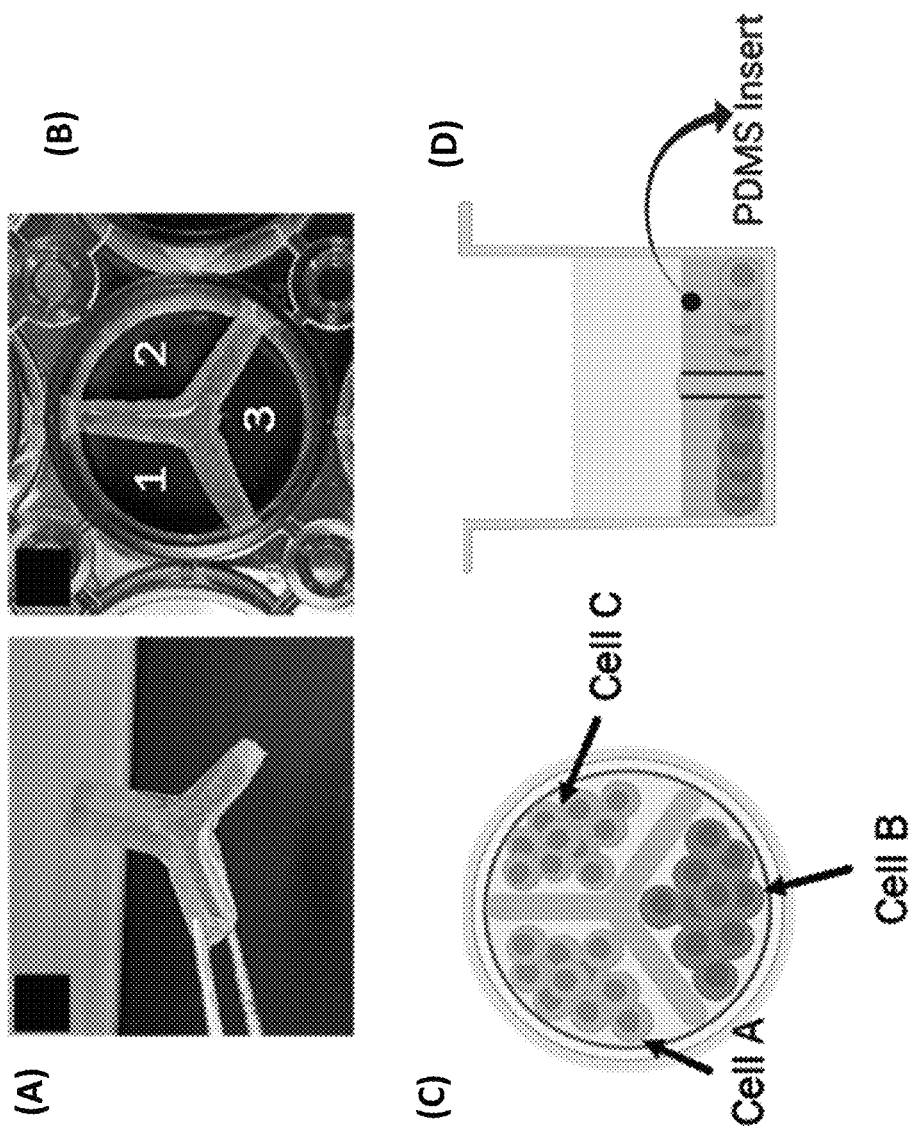
FIG. 2 shows an embodiment of the disclosure. (A) shows a branched insert; (B) shows the top view of the branched insert in a well. (C) shows a top view of the well with three different cell populations and (D) show the side view of (C).
Figure 3:
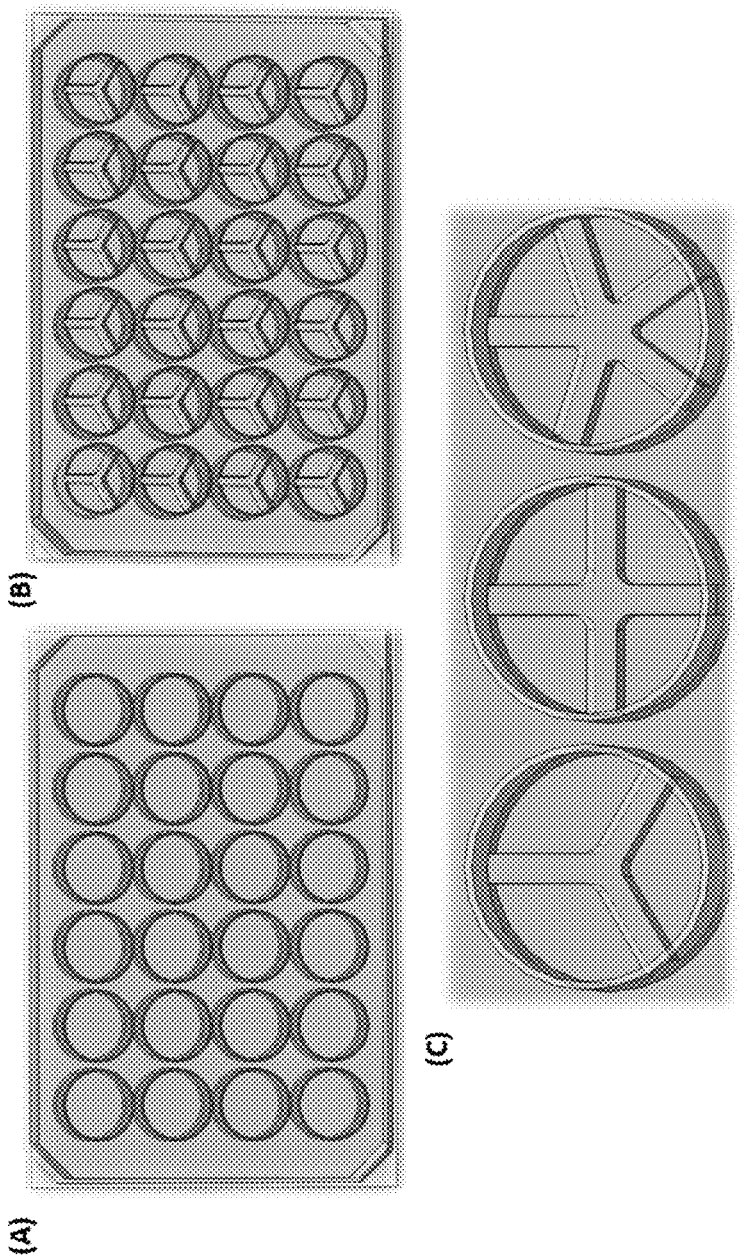
FIG. 3 shows new modalities of the multi-chamber culture system which can be done by modifying the standard design of the well-plate through the integration of the dividing branches at the bottom of its wells. (A) Standard 24 well plate, (B) modified 24-well plate with the new tri-culture system modality, and (C) an example showing how the design of the tri-culture system can be modified to occupy more than three cell population within the same well (e.g., 4 or 5 cell populations).

Live/dead images showed that cells exhibited high viability at both time points (FIG. 3A). Proliferation assay showed that the three different cell types were able to proliferate within their respective regions and showed significantly higher proliferation at day 7 when compared to day 3 (FIG. 10B). Generally, fibroblasts at regions A and B showed higher proliferation when compared to OB at region C at both time points, most likely because of the difference in proliferation rates between fibroblasts and osteoblasts[26].

The three different cell types showed strong expression to the protein actin at both times as confirmed by the actin staining images (FIG. 10G). As cells substantially proliferated after 7 days, basal actin filaments were observed to be entirely interconnected and formed orthogonal networks on the surface of the different regions, indicating that the cells were able to fully spread and migrate to different parts within their respective regions. Although the pore volume at region C was filled with gelatin-mTG hydrogel, OBs were observed to have spread cell morphology throughout the region with robust cell migration at deeper regions, indicating that the presence of the hydrogel matrix did not hinder their spreading nor infiltration at this region.

Immunofluorescent images showed that cells in all regions were able to maintain their phenotype during the heterogeneous culture at both time points, as confirmed by the positive expression seen to their specific proteins (FIG. 10C). At day 7, all cells showed significantly higher expression to their specific proteins compared to day 3, indicating that these proteins were still able to be produced as cells were proliferating over time in the heterogeneous environment (FIG. 10D). Fibroblasts in both regions A and B were also immuno-stained with ALP to evaluate whether the paracrine factors mediated by OBs during the heterogeneous culture could induce their osteogenic differentiation. Both SFs and STFs in regions A and B did not show any expression to ALP at both time points (FIG. 10E,F) indicating that the paracrine factors mediated by OBs during the heterogeneous culture did not have stimulatory effects on both fibroblasts phenotypes, likely due to relevant biomimetic structural cues provided within the CGS which promoted their phenotypic maintenance.

Previous literature has shown hindered physiological functions and phenotypic characteristics of both SFs and STFs when co-cultured with OBs in a monolayer-based co-culture systems[22,23,24]. The current study shows that combining the three different cell phenotypes in a physiologically relevant 3D microenvironment can rapidly maintain their relative physiological functions and phenotypic characteristics during the heterogeneous culture. These data imply the effectiveness of the CGS to act as a physiologically relevant milieu for studying different cell responses to heterogeneous culture. In addition, data indicate that the surrounding microenvironment plays a key role in modulating the cellular behavior during the heterogeneous culture and that conclusions derived from 2D monolayer-based culture systems are not reliable due to the lack of recapitulation of the tissue and organ-level structures and functions that are central for modulating biomimetic cellular responses.

Achieving Bioactive CGS by Locally Presenting Different Tissue-Mediated Growth Factors in a Region-Specific Manner.

The feasibility of the CGS to act as a bioactive milieu by simultaneously enabling the presentation of different growth factors to achieve enhanced cell response while maintaining distinct cellular regions was investigated. This was achieved by incorporating different tissue-mediated growth factors in the three different regions. Specifically, ~1 μg of rhPDGF-BB, rhIGF-I, and rhBMP-2 were incorporated into regions A, B, and C, respectively. This resulted in a spatial and local presentation of growth factors throughout the CGS in a region-specific manner.

Since the CGS consists of heterogeneous cell phenotypes, it was essential that the release of the incorporated factors from each region was tuned to avoid any potential undesirable effects that may occur due to improper singling. Therefore, the incorporation mechanism of the three growth factors into their respective regions (physical vs. immobilization) was determined based on their biological effects on the other cell phenotypes within the CGS. For instance, due to the mitogenic effects of both rhPDGF-BB and rhIGF-I on SFs, STFs, and OBs[27, 28, 29, 30, 31, 32], they were physically incorporated into the core-shell of the nanofibers of both regions A and B, respectively. This resulted in a sustained and prolonged release over the incorporated factors for 14 days (FIG. 11A), which suggests that they were locally being released within the domain of their respective regions. In contrast, due to the morphogenetic and osteoinductive effects of rhBMP-2 on both SFs and STFs[33-35], it was immobilized by covalently binding it to the gelatin-mTG hydrogel matrix within region C to avoid its potential exposure to both fibroblasts phenotypes. Covalently binding rhBMP-2 resulted in its complete retention within region C, as no evidence for rhBMP-2 release was observed for 14 days (FIG. 11A). rhBMP-2 incorporated into the gelatin hydrogel was completely retained upon the addition of mTG due to the covalent bonding initiated between rhBMP-2 and gelatin as a result of the enzymatic crosslinking by mTG[19].

To confirm the retention of rhBMP-2 the same samples used during the release study were subjected to digestion by incubation in collagenase type I solution to digest the gelatin-mTG matrix within region C in order to allow the retained protein to release, followed by measuring the amount of the released rhBMP-2 in the supernatant. The average total retained rhBMP-2 in all samples was found to be 967.5±205 ng (FIG. 11B), indicating its successful retention.

Figure 11:
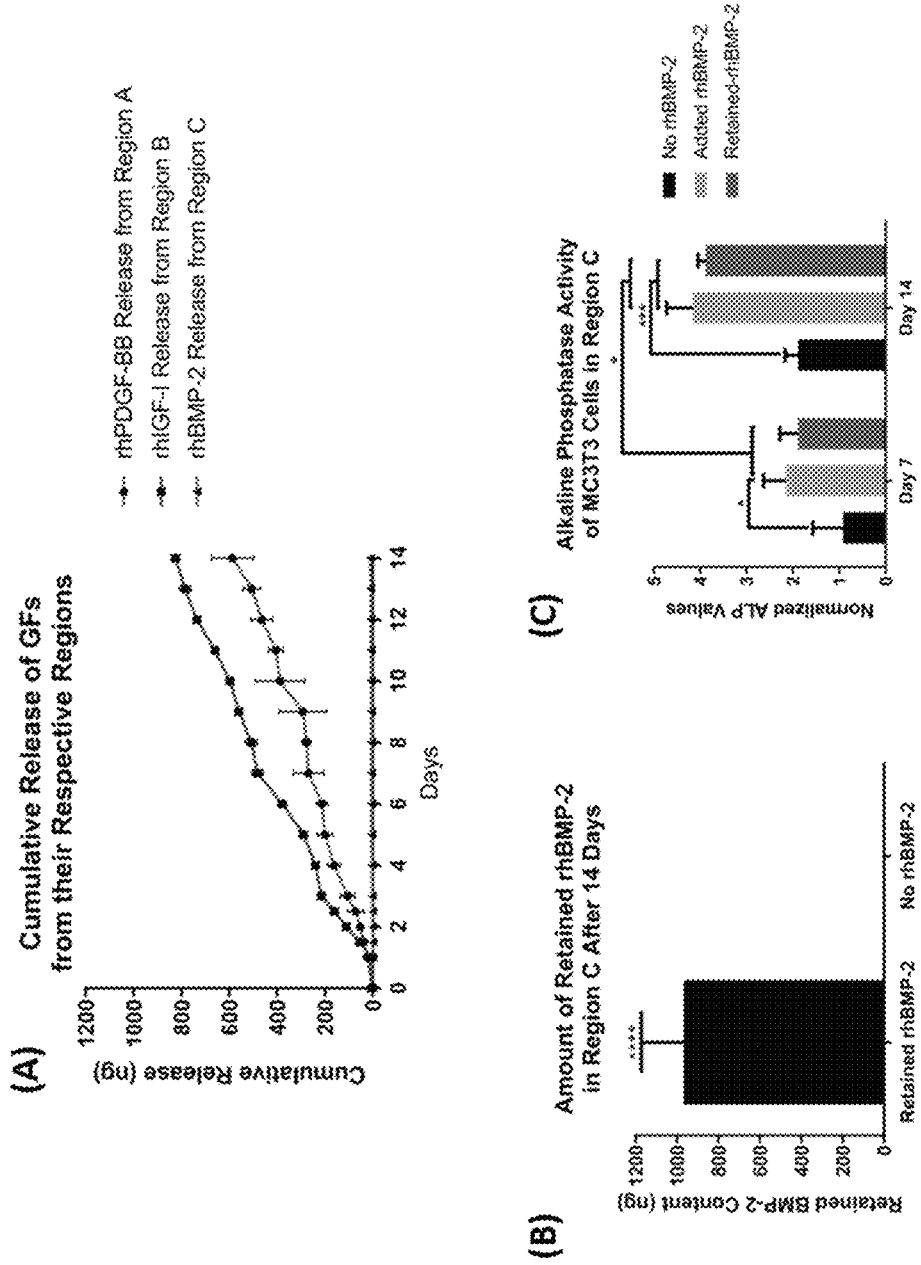
FIG. 11 shows the cumulative release patterns of different growth factors incorporated into the different regions. Approximately 1 µg (1000 ng) of each growth factor was incorporated into the corresponding regions, followed by incubating them separately in PBS at 37° C. and monitoring their release pattern for 14 days. (A) rhPDGF-BB, rhIGF-I and BMP-2 release patterns from regions A, B and C, respectively. Coaxial nanofibers of both regions A and B could sustain and prolong the release of both rhPDGF-BB and rhIGF-I for 14 days. However, no evidence for rhBMP-2 release was observed during the 14 days study period, indicating the retention of rhBMP-2 in the gelatin-mTG hydrogel in region C. (B) To confirm the retention of rhBMP-2 in region C the same samples used during the release study were incubated in collagenase solution to digest the hydrogel matrix for rhBMP-2 extraction. Most of the protein was retained in all of the assayed samples with an average total retained protein of 967.5±205 ng. (C) To evaluate the bioactivities of the retained rhBMP-2, MC3T3 cells where seeded on region C for 14 days and assayed for change in ALP activates. The retained rhBMP-2 stimulated MC3T3 cells to secrete higher levels of ALP after 14 days when compared to the negative control, indicating that rhBMP-2 is bioactive when retained.

To examine the bioactivity of the retained rhBMP-2 we measured the ALP activity of MC3T3 cells seeded on region C for 14 days and compared the results to region C-free of rhBMP-2 (negative control), and region C-free of rhBMP-2 with rhBMP-2 added to the culture medium (positive control). Data revealed that the MC3T3 cells showed significantly higher ALP levels at day 14 on both the experimental and the positive control groups when compared to the negative control, indicating that the retention of rhBMP-2 does not eliminate its bioactivity (FIG. 11C).

Previous studies have shown that growth factors covalently bonded in enzymatically crosslinked hydrogels only start releasing upon the degradation of the hydrogel matrix[36]. Because the release study here was carried out in phosphate-buffered saline (PBS), no release of the bonded rhBMP-2 was observed. Enzymatically crosslinked hydrogels only degrade when they are exposed to degrading enzymes such as collagenase or degrading enzymes endogenously secreted by cells[36]. When the retained rhBMP-2 in region C was examined for its bioactivity the ALP levels of the seeded MC3T3 cells were significantly elevated compared to the negative control at day 14. This suggests that the bonded rhBMP-2 was able to release and stimulate the cells due to the degradation of the gelatin-mTG matrix by the degrading enzymes endogenously secreted by the cells.

While surface immobilization has been shown to be an effective technique for localizing growth factors in a region-specific manner[37], here, the physical incorporation of both rhPDGF-BB and rhIGF-I into regions A and B, as well as the retention of rhBMP-2 in the gelatin-mTG matrix within region C techniques were favored over immobilizing them at the surface of their respective regions for three reasons; (1) The amount of the loaded protein using the techniques used herein can be controlled compared to the surface immobilization technique, (2) The amount of the physically incorporated or retained protein is often larger than when they are surface-immobilized, as the amount of the surface-immobilized protein is limited by the surface area of the construct as well as the binding affinity/efficiency, and (3) Physically incorporated or retained proteins are continuously exposed to the cells for a prolonged period of time due to the continuous release of the loaded protein, whereas cells seeded on surface-immobilized protein based-construct are only limited to the amount of protein present on the surface of the construct that soon diminishes upon the subsequent degradation of the surface of the construct.

Spatial Localization of Growth Factors in a Region-Specific Manner within the CGS Resulted in Heterogeneity Maintenance and Enhanced Cell Functions During a Heterogeneous Culture In Vitro.

Figure 12:
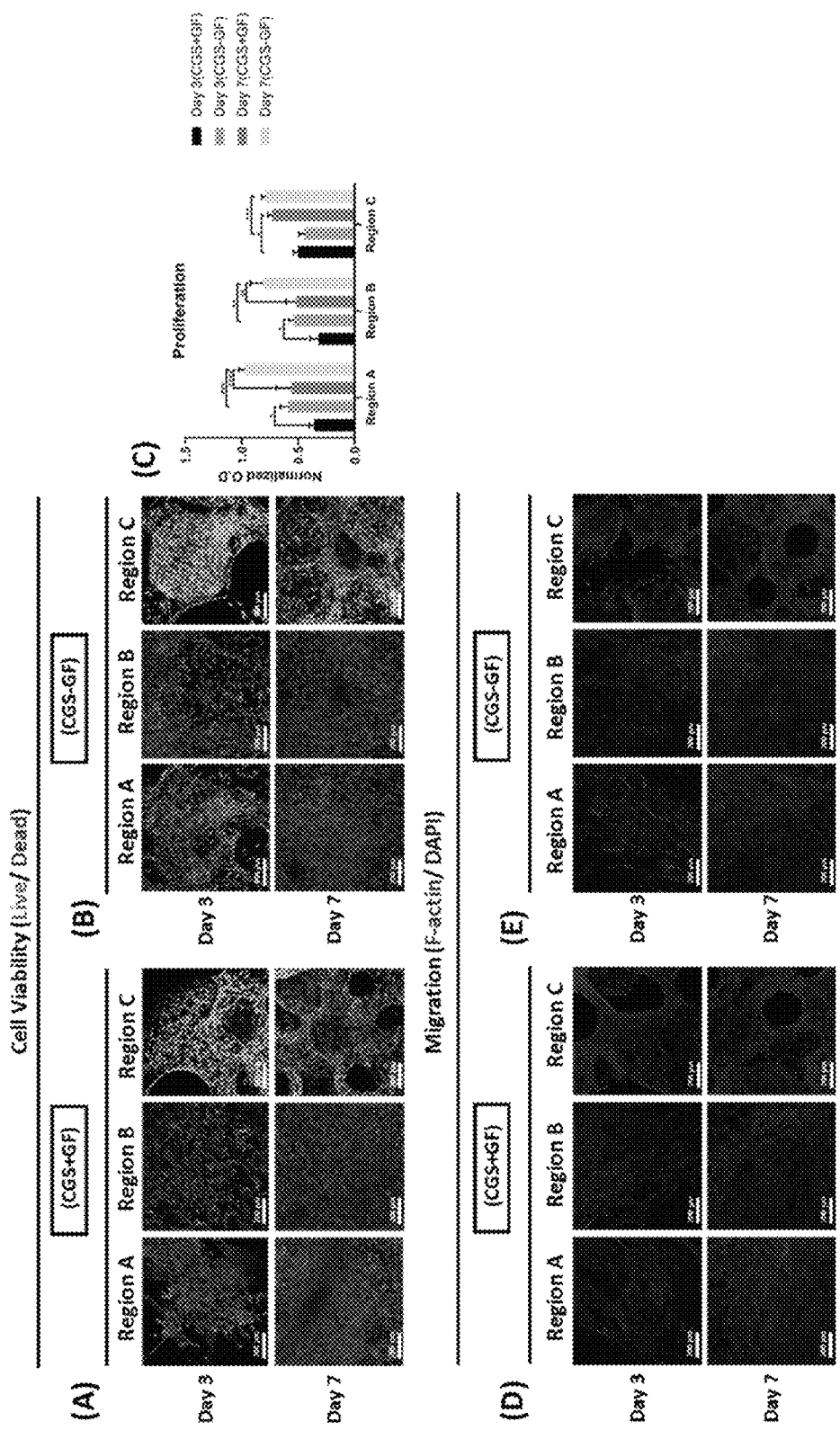
FIG. 12 shows effects of growth factor presentation mode on SFs, STFs and OBs viability, proliferation and migration during a heterogeneous culture. (A) Representative live/dead stained images for regions A, B and C in the CGS+GF and (B) CGS–GF groups at 3 and 7 days. (C) Proliferation of SF, STF and OB in regions A, B and C, respectively in the CGS+GF and CGS-GF groups at 3 and 7 days. (D) Representative F-actin staining images for regions A, B and C in the CGS+GF and (E) CGS-GF groups at 3 and 7 days.

The cells' response to the growth factors addition into the CGS was evaluated in two different ways. 1) We first evaluated the role of the growth factors presentation mode on the different cells' response during the heterogeneous culture. Here, growth factors were either specially localized into their respective regions within the graft system (CGS-GF), as discussed in the previous section or directly added to the growth medium during the culture time (CGS+GF) and the effects of the growth factors presentation mode on the physiological functions and the phenotypic characteristics of the different cell phenotypes in both groups were evaluated at 3 and 7 days. We found that in both groups the different cells maintained high viability at both time points (FIG. 12A,B) but proliferated differently (FIG. 12C). In the CGS+GF group, the proliferation of fibroblasts in both regions A and B was significantly suppressed at both time points compared to those in the CGS-GF group, which showed significantly higher proliferation. At day 7, fibroblasts in both regions A and B in the CGS-GF group showed significantly higher proliferation compared to day 3, but no statistically significant difference was found in those cultured in the CGS+GF between both time points. OBs in region C showed similar proliferation in both groups at days 3 and 7 with no statistically significant difference. At day 7, OBs in both groups showed significantly higher proliferation compared to their proliferation at day 3.

Interestingly, cells in all regions from both groups showed similar actin expression and filaments morphology at both time point as confirmed by the actin staining images with no significant differences (FIG. 12 D,E), indicating that cells in both groups were able to spread and migrate similarly within their respective regions regardless of the growth factors presentation mode.

Figure 13:
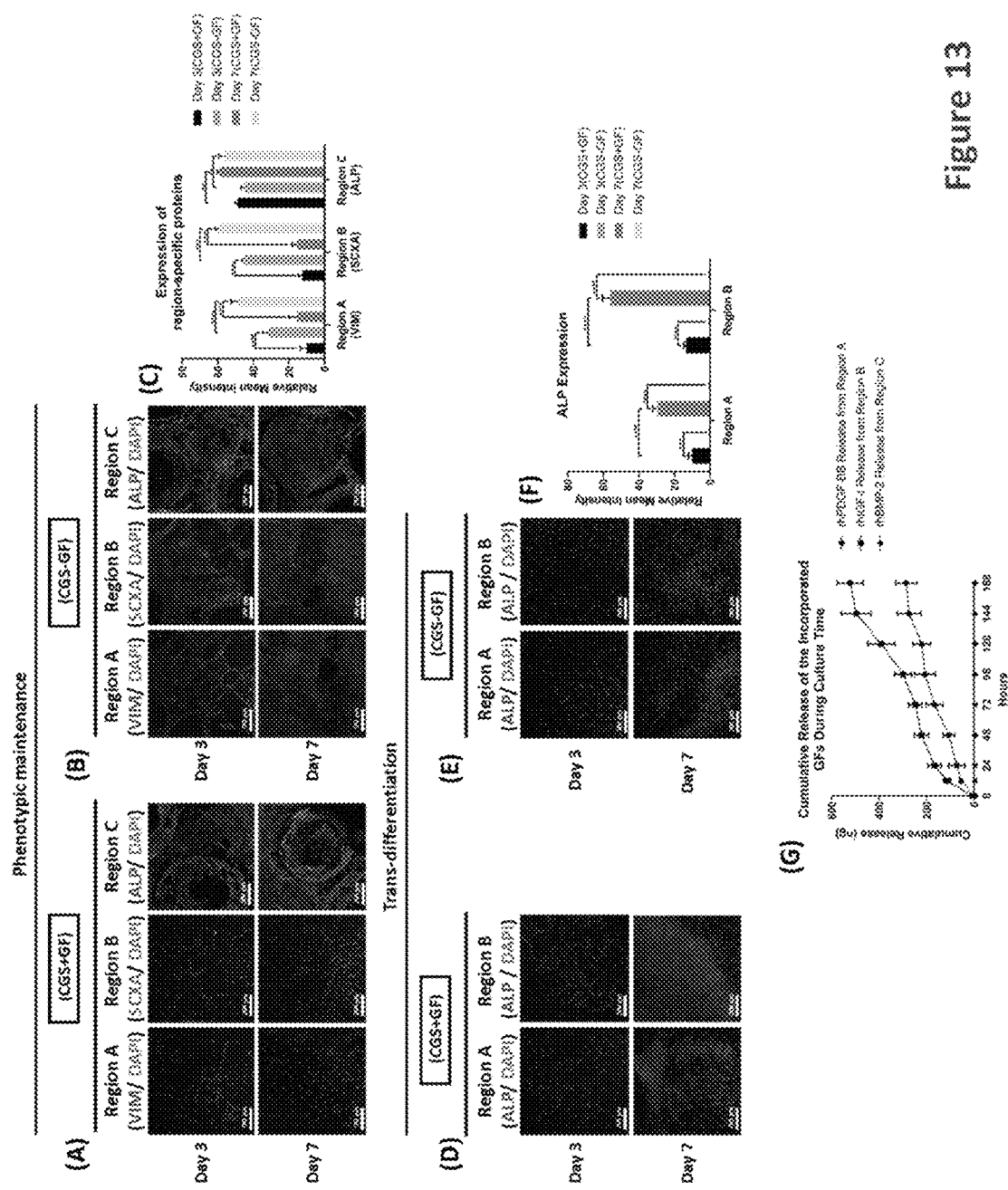
FIG. 13 shows effects of growth factor presentation mode on the phenotypic characteristics of SFs, STFs and OBs during a heterogeneous culture. (A) Immunofluorescent staining of regions A, B and C for VIM, SCXA and ALP, respectively in the CGS+GF and (B) CGS-GF groups at 3 and 7 days and (C) quantifications of VIM, SCXA and ALP expression from regions A, B and C in the CGS+GF and CGS–GF groups at 3 and 7 days. (D) Immunofluorescent staining of regions A and B for ALP in the CGS+GF and (E) CGS–GF groups at 3 and 7 days and (F) quantifications of ALP expression from regions A and B in the CGS+GF and CGS-GF groups at 3 and 7 days. (G) The cumulative release of the incorporated growth factors from the CGS-GF group during 7 days of culture.

Immunofluorescent images revealed that cells in regions A, B, and C in the CGS-GF group were able to maintain their phenotype as they were strongly positive for VIM, SCAX and ALP, respectively, at both time points (FIG. 13B) with a significant increase in expression at day 7 compared to day 3 (FIG. 13C). In contrast, only OBs in the CGS+GF group were able to show phenotypic maintenance ability at both time points with significantly higher ALP expression at day 7 compared to day 3 (FIG. 12A) and quantification data (FIG. 13C). There was no statistically significant difference in OBs ALP expression between CGS-GF and CGS+GF groups at both time points (FIG. 13C).

Both fibroblast phenotypes in regions A and B showed a significant reduction in the expression of their fibroblastic specific markers at both time points in the CGS+GF group compared to the CGS-GF group (FIG. 13A,B), with no statistical difference observed between days 3 and 7 (FIG. 13C). We attribute this to their direct exposure to rhBMP-2 upon its direct and uncontrolled presentation in this group, which may have caused trans-differentiation of both fibroblast phenotypes to an osteogenic lineage, owing to its osteoinductive effects[33-35]. This also explains the significant reduction seen in the proliferation of both fibroblast phenotypes in this group as cells tend to exit the division cycle as they undergo differentiation[38].

To validate these findings, we evaluated the expression of ALP in both regions A and B by immunofluorescent staining at 3 and 7 days in both groups. Only SFs and STFs in the CGS+GF showed positive expression to ALP that significantly increased with time in comparison to the same cell phenotypes in the CGS-GF group, which showed no expression to ALP at both time points (FIG. 13D,E,F). To further confirm these findings, we measured the cumulative release of the incorporated growth factors in the CGS-GF group during the 7 days culture period. Measuring the cumulative release during the culture time was essential to confirm that rhBMP-2 was still completely retained within region C and that the endogenously secreted degrading enzymes by cells in region C are not causing it to be released to the culture medium. We found that only rhPDGF-BB and rhIGF-I released during the 7 days, while no evidence for rhBMP-2 release was observed (FIG. 13G), indicating its complete retention even during the culture time, and suggesting that the release of rhBMP-2 was within a limited domain, sufficient enough to only stimulate cells that are in close proximity or direct contact to the gelatin-mTG matrix within region C. This indicates that both fibroblast phenotypes were not being exposed to rhBMP-2 during the culture period, further elucidating the phenotypic maintenance of fibroblasts observed in this group in comparison to the CGS+GF group. Although both fibroblast phenotypes in the CGS-GF group were simultaneously being exposed to rhPDGF-BB and rhIGF-I during the culture period as evidenced by the release data (FIG. 13G), they were still able to maintain their relative heterogeneity. rhPDGF-BB and rhIGF-I are mitogenic factors that do not elicit any phenotypic modulatory effects on SFs or STFs[27, 28, 29, 30]. In fact, they both were shown to have synergetic effects in promoting the physiological functions of both SFs and STFs[29,30]. This further confirms that the only factor that caused the phenotypic alteration of both fibroblast phenotypes seen in the CGS+GF group was their direct exposure to rhBMP-2. In other words, if only rhPDGF-BB and rhIGF-I were to be added to the culture medium in the CGS+GF group, SFs and STFs would have been able to maintain their relative heterogeneity.

Figure 16:
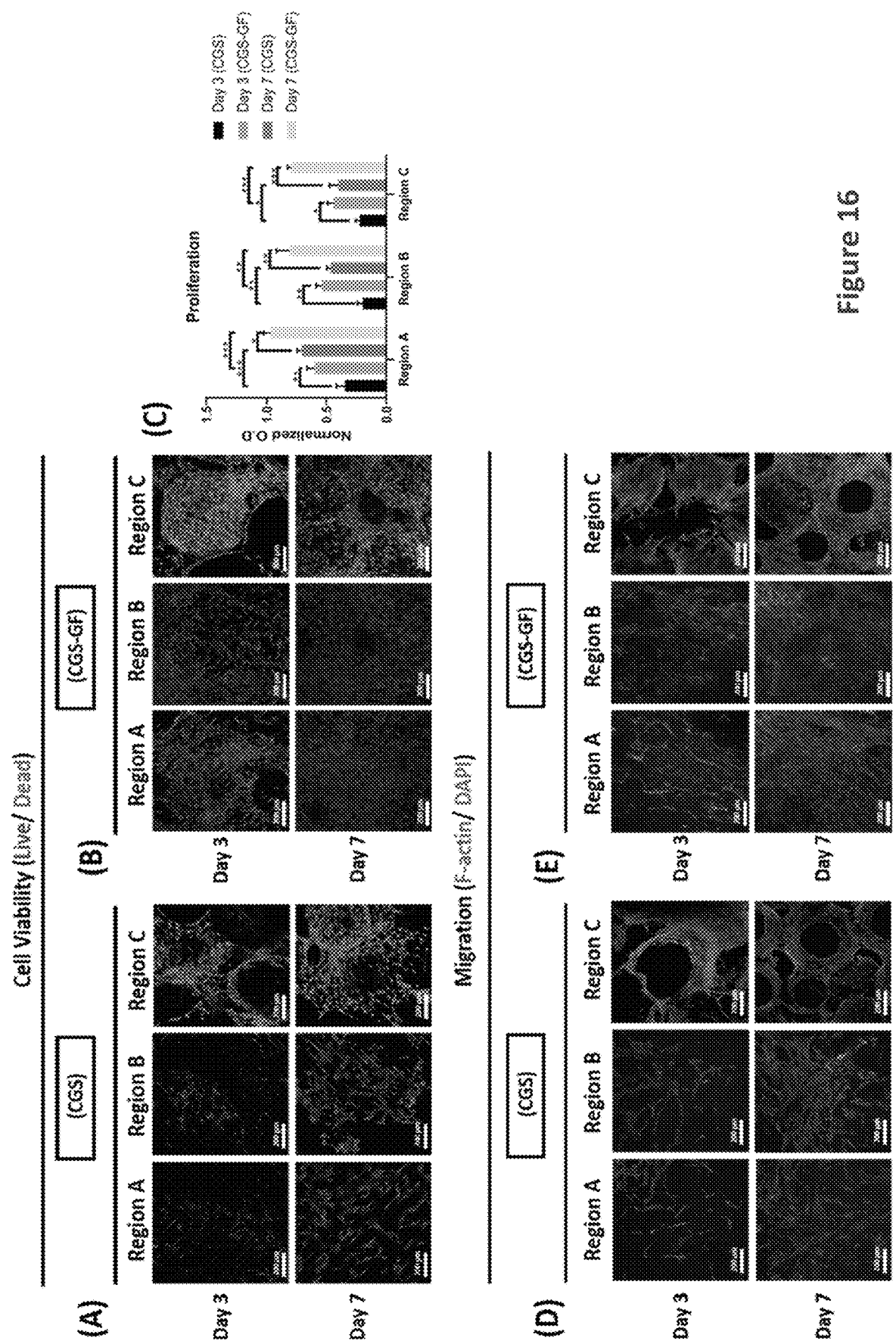
FIG. 16 shows A direct comparison between CGS and CGS-GF highlighting the effects of growth factors addition on the region-specific cell viability, proliferation and migration during the heterogeneous culture. (A) Representative live/dead stained images for regions A. B and C in the CGS and (B) CGS-GF groups at 3 and 7 days (n=3, and 4-6 random fields/sample). (C) Proliferation of SFs, STFs, and OBs in regions A, B and C, respectively in the CGS and CGS-GF groups at 3 and 7 days (n=3, ANOVA and post hoc Tukey test, *P<0.05, P<0.01, *P<0.001). (D) Representative F-actin staining images for regions A, B and C in the CGS and (E) CGS-GF groups at 3 and 7 days (n=3, and 4-6 random fields/sample).
Figure 17:
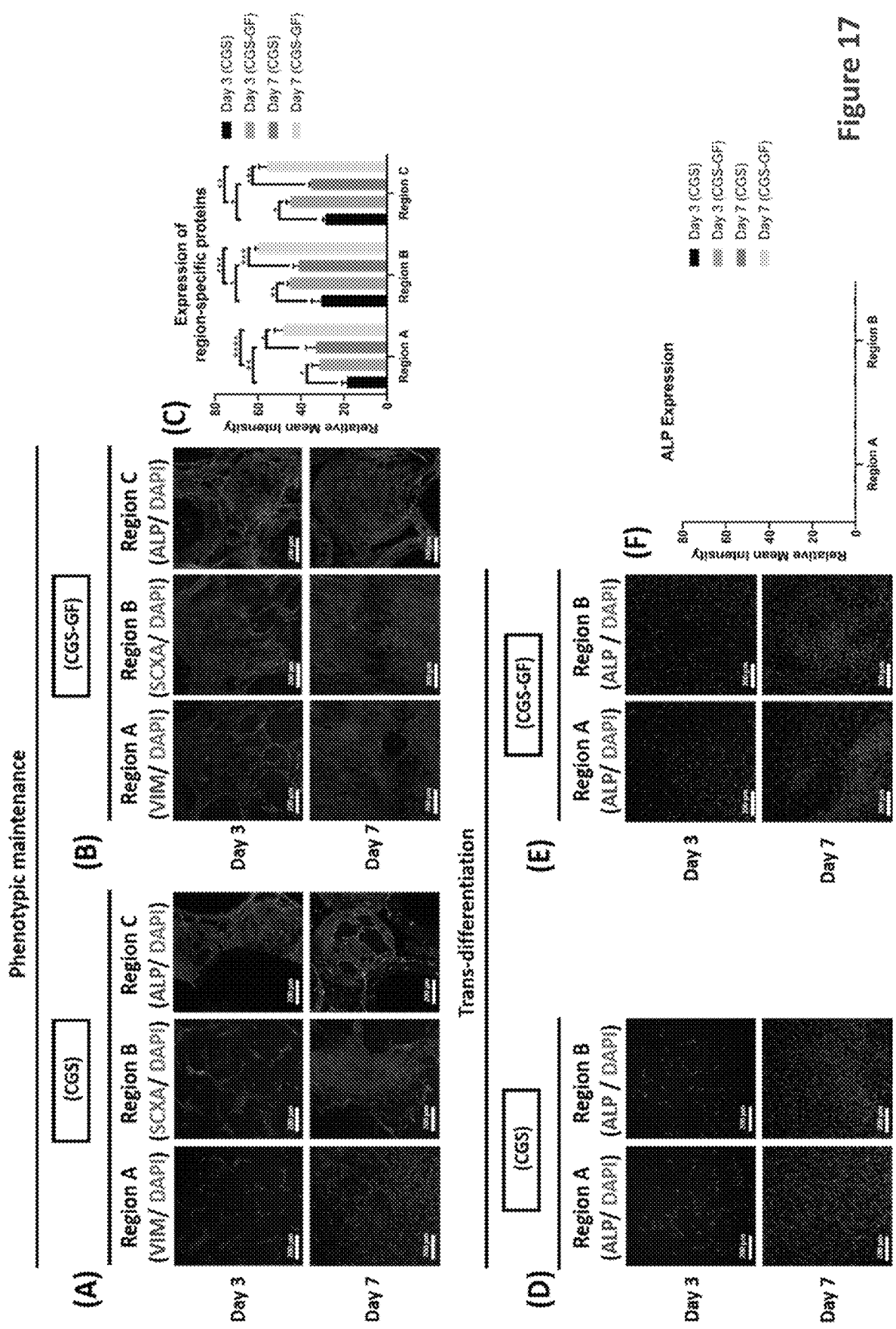
FIG. 17 A direct comparison between CGS and CGS-GF highlighting the effects of growth factors addition on the region-specific protein expression levels and phenotypic maintenance during the heterogeneous culture. (A) Immunofluorescent staining of regions A, B, and C for VIM, SCXA, and ALP, respectively in the CGS and (B) CGS-GF groups at 3 and 7 days and (C) quantifications of VIM, SCXA and ALP expression from regions A, B and C in the CGS and CGS-GF groups at 3 and 7 days (n=3, and 4-6 random images/sample, ANOVA and post hoc Tukey test, *P<0.05, P<0.01, *P<0.001, ****P<0.0001). (D) Immunofluorescent staining of regions A and B for ALP in the CGS and (E) CGS-GF groups at 3 and 7 days and (F) quantifications of ALP expression from regions A and B in the CGS and CGS-GF groups at 3 and 7 days (n=3, and 4-6 random images/sample, ANOVA and post hoc Tukey test).

We next evaluated the effects of the growth factors themselves on the different cells' performance in this system by making a direct comparison between the CGS and CGS-GF to investigate whether the spatial presentation of growth factors is enhancing the different cells' performance during the heterogeneous culture. We found that not only the spatial presentation of growth factors within the graft system could maintain the different cells' phenotype (FIG. 17), but also significantly enhanced the region's-specific protein expression (FIG. 17A, B, C), viability (FIG. 16A, B), and physiological functions such as proliferation and migration (FIG. 16C, D, E), demonstrating the feasibility of the graft system to act as a bioactive milieu and its ability to control the presentation of different growth factors simultaneously for directing specific cell responses in a region-specific manner.

Collectively, these data provide evidence that CGS is a reliable tool that can be utilize for investigating different cell responses due to its closer resemblance to the native in vivo milieu. This includes but not limited to the investigation of the responses of distinct population of cells to paracrine interactions during a heterogenous culture. Moreover, data showed the feasibility of the CGS to act as a bioactive milieu and its ability to control the presentation of different growth factors simultaneously for directing specific cell responses by localizing the presentation of growth factors in a region-specific manner. We showed that the region-specific localization of growth factors, particularly those that elicit phenotypic modulatory effects on other cell phenotypes such as rhBMP-2, is crucial to enhance and maintain the different cells' relative physiological functions and phenotypic characteristics during a heterogeneous culture in a single construct. This implies that the CGS presented herein could also be used as a platform for studying different approaches for simultaneously delivering multiple growth factors or molecules on a single construct to achieve enhanced cell response while maintaining cellular heterogeneity during heterogenous culture.

REFERENCES FOR ABOVE EXAMPLE

1. Ma, Z., Kotaki, M., Yong, T., He, W. & Ramakrishna, S. Surface engineering of electrospun polyethylene terephthalate (PET) nanofibers towards development of a new material for blood vessel engineering. *Biomaterials* 26, 2527-2536 (2005).
2. Sahoo, S., Ang, L. T., Goh, J. C.-H. & Toh, S.-L. Growth factor delivery through electrospun nanofibers in scaffolds for tissue engineering applications. *J Biomed Mater Res A* 93, 1539-1550 (2010).
3. Stern, A. R. et al. Isolation and culture of primary osteocytes from the long bones of skeletally mature and aged mice. *BioTechniques* 52, 361-373 (2012).
4. Lyon, R. M., Akeson, W. H., Amiel, D., Kitabayashi, L. R. & Woo, S. L. Ultrastructural differences between the cells of the medical collateral and the anterior cruciate ligaments. *Clin. Orthop. Relat. Res.* 279-286 (1991).
5. Seluanov, A., Vaidya, A. & Gorbunova, V. Establishing Primary Adult Fibroblast Cultures From Rodents. *J Vis Exp* (2010) doi:10.3791/2033.
6. Park, P. I. P. & Jonnalagadda, S. Predictors of glass transition in the biodegradable poly-lactide and poly-lactide-co-glycolide polymers. *Journal of Applied Polymer Science* 100, 1983-1987 (2006).
7. Gentile, P., Chiono, V., Carmagnola, I. & Hatton, P. V. An Overview of Poly(lactic-co-glycolic) Acid (PLGA)-Based Biomaterials for Bone Tissue Engineering. *Int J Mol Sci* 15, 3640-3659 (2014).
8. Liu, M., Duan, X.-P., Li, Y.-M., Yang, D.-P. & Long, Y.-Z. Electrospun nanofibers for wound healing. *Materials Science and Engineering. C* 76, 1413-1423 (2017).
9. Sensini, A. & Cristofolini, L. Biofabrication of Electrospun Scaffolds for the Regeneration of Tendons and Ligaments. *Materials (Basel)* 11, (2018).
10. Saveh-Shemshaki, N., S Nair, L. & Laurencin, C. T. Nanofiber-based matrices for rotator cuff regenerative engineering. *Acta Biomater* 94, 64-81 (2019).
11. Lu, Y. et al. Coaxial electrospun fibers: applications in drug delivery and tissue engineering. *Wiley Interdiscip Rev Nanomed Nanobiotechnol* 8, 654-677 (2016).
12. Buzgo, M., Mickova, A., Rampichova, M. & Doupnik, M. 11—Blend electrospinning, coaxial electrospinning, and emulsion electrospinning techniques. in *Core-Shell Nanostructures for Drug Delivery and Theranostics* (eds. Focarete, M. L. & Tampieri, A.) 325-347 (Woodhead Publishing, 2018). doi:10.1016/B978-0-08-102198-9.00011-9.
13. Borden, M., Attawia, M. & Laurencin, C. T. The sintered microsphere matrix for bone tissue engineering: in vitro osteoconductivity studies. *J. Biomed. Mater. Res.* 61, 421-429 (2002).
14. Jiang, T., Khan, Y., Nair, L. S., Abdel-Fattah, W. I. & Laurencin, C. T. Functionalization of chitosan/poly(lactic acid-glycolic acid) sintered microsphere scaffolds via surface heparinization for bone tissue engineering. *Journal of Biomedical Materials Research Part A* 93A, 1193-1208 (2010).
15. Jiang, T. et al. Chitosan-poly(lactide-co-glycolide) microsphere-based scaffolds for bone tissue engineering: in vitro degradation and in vivo bone regeneration studies. *Acta Biomater* 6, 3457-3470 (2010).
16. Echave, M. C., Saenz del Burgo, L., Pedraz, J. L. & Orive, G. Gelatin as Biomaterial for Tissue Engineering. *Curr. Pharm. Des.* 23, 3567-3584 (2017).
17. Asamura, S., Mochizuki, Y., Yamamoto, M., Tabata, Y. & Isogai, N. Bone regeneration using a bone morphogenetic protein-2 saturated slow-release gelatin hydrogel sheet: evaluation in a canine orbital floor fracture model. *Ann Plast Surg* 64, 496-502 (2010).
18. Yamamoto, M., Ikada, Y. & Tabata, Y. Controlled release of growth factors based on biodegradation of gelatin hydrogel. *J Biomater Sci Polym Ed* 12, 77-88 (2001).
19. Kuwahara, K., Fang, J. Y., Yang, Z. & Han, B. Enzymatic crosslinking and degradation of gelatin as a switch for bone morphogenetic protein-2 activity. *Tissue Eng Part A* 17, 2955-2964 (2011).
20. Katti, D. S., Robinson, K. W., Ko, F. K. & Laurencin, C. T. Bioresorbable nanofiber-based systems for wound healing and drug delivery: optimization of fabrication parameters. *J. Biomed. Mater. Res. Part B Appl. Biomater.* 70, 286-296 (2004).
21. Amini, A. R., Adams, D. J., Laurencin, C. T. & Nukavarapu, S. P. Optimally Porous and Biomechanically Compatible Scaffolds for Large-Area Bone Regeneration. *Tissue Eng Part A* 18, 1376-1388 (2012).
22. Wang, I.-N. E. et al. Role of osteoblast-fibroblast interactions in the formation of the ligament-to-bone interface. *J. Orthop. Res.* 25, 1609-1620 (2007).
23. Janardhanan, S., Wang, M. O. & Fisher, J. P. Coculture Strategies in Bone Tissue Engineering: The Impact of Culture Conditions on Pluripotent Stem Cell Populations. *Tissue Eng Part B Rev* 18, 312-321 (2012).
24. Pirraco, R. P., Cerqueira, M. T., Reis, R. L. & Marques, A. P. Fibroblasts regulate osteoblasts through gap junctional communication. *Cytotherapy* 14, 1276-1287 (2012).
25. Yao, T. & Asayama, Y. Animal-cell culture media: History, characteristics, and current issues. *Reprod Med Biol* 16, 99-117 (2017).
26. Spalazzi, J. P., Doty, S. B., Moffat, K. L., Levine, W. N. & Lu, H. H. Development of controlled matrix heterogeneity on a triphasic scaffold for orthopedic interface tissue engineering. *Tissue Eng.* 12, 3497-3508 (2006).
27. Li, W. et al. Mechanism of Human Dermal Fibroblast Migration Driven by Type I Collagen and Platelet-derived Growth Factor-BB. *Mol Biol Cell* 15, 294-309 (2004).
28. Kobayashi, K. et al. Effect of insulin-like growth factor 1 and basic fibroblast growth factor on DNA synthesis and collagen production in cultured anterior cruciate ligament cells. *J Orthop Sci* 2, 349-356 (1997).
29. Grazul-Bilska, A. T. et al. Wound healing: the role of growth factors. *Drugs Today* 39, 787-800 (2003).
30. Gamal, A. Y., Mailhot, J. M., Garnick, J. J., Newhouse, R. & Sharawy, M. M. Human periodontal ligament fibroblast response to PDGF-BB and IGF-1 application on tetracycline HCl conditioned root surfaces. *J. Clin. Periodontol.* 25, 404-412 (1998).
31. Canalis, E., McCarthy, T. L. & Centrella, M. Effects of platelet-derived growth factor on bone formation in vitro. *Journal of Cellular Physiology* 140, 530-537 (1989).
32. Lynch, S. E. et al. Effects of the platelet-derived growth factorinsulin-like growth factor-combination on bone regeneration around titanium dental implants. Results of a pilot study in beagle dogs. *J. Periodontol.* 62, 710-716 (1991).

33. Yang, J. et al. Bone morphogenetic proteins: Relationship between molecular structure and their osteogenic activity. *Food Science and Human Wellness* 3, 127-135 (2014).
34. Si, X. & Liu, Z. [The biological effects of recombinant human bone morphogenetic protein 2 on human periodontal ligament fibroblasts]. *Hua Xi Kou Qiang Yi Xue Za Zhi* 20, 10-13 (2002).
35. Myllyl, R. M., Haapasaari, K.-M., Lehenkari, P. & Tuukkanen, J. Bone morphogenetic proteins 4 and 2/7 induce osteogenic differentiation of mouse skin derived fibroblast and dermal papilla cells. *Cell Tissue Res.* 355, 463-470 (2014).
36. Ikada, null & Tabata, null. Protein release from gelatin matrices. *Adv. Drug Deliv. Rev.* 31, 287-301 (1998).
37. Lee, K., Silva, E. A. & Mooney, D. J. Growth factor delivery-based tissue engineering: general approaches and a review of recent developments. *J R Soc Interface* 8, 153-170 (2011).
38. Ruijtenberg, S. & van den Heuvel, S. Coordinating cell proliferation and differentiation: Antagonism between cell cycle regulators and cell type-specific gene expression. *Cell Cycle* 15, 196-212 (2016).

We claim:

1. A cell culture system comprising:
   a. a culture plate comprising at least one well, wherein each well comprises a bottom and a wall having a height, and
   b. one or more branched non-permeable inserts,
      i. wherein each well contains no more than one branched non-permeable insert;
      ii. wherein each branched non-permeable insert comprises three or more branches; and
      iii. wherein each non-permeable insert divides a bottom portion of the well into three or more chambers, wherein each non-permeable insert does not divide the entire top portion of the height of the well, and
         A. wherein each non-permeable insert is capable of preventing physical interaction between cell populations in different chambers in a well, and
         B. wherein each non-permeable insert is capable of permitting chemical signaling between cell populations in different chambers in a well.

2. The system of claim 1, wherein the each branched non-permeable insert divides the bottom portions of the well into four, five or six chambers.

3. The system of claim 1, wherein the each branched non-permeable insert comprises a cured polymer.

4. The system of claim 3, wherein the cured polymer comprises polydimethylsiloxane (PDMS).

5. The system of claim 1, wherein the each branched non-permeable insert adheres to the well.

6. The system of claim 1, wherein each branched non-permeable insert is permanently integrated within the well.

7. The system of claim 6, wherein each branched non-permeable insert comprises the same material as the culture plate.

8. The system of claim 6, wherein each branched non-permeable insert comprises polystyrene.

9. The system of claim 1, wherein dimensions of each branched non-permeable insert allows the one or more branched non-permeable insert to be used in a commercially available culture plate.

10. The system of claim 1, where in the culture plate is selected from the group consisting of 6-well plates, 12-well plates, 24-well plates, 36-well plates, 48-well plates, and 96-well plates.

11. The system of claim 1, wherein each chamber comprises substantially identical volume, dimensions, and geometry.

12. A method for culturing multiple cell populations comprising:
    a. adding a cell population into each individual chamber in a single well of the system of claim 1;
    b. adding culture media to the well; and
    c. incubating the culture plate.

13. The method of claim 12, wherein the cell population added into each individual chamber is a different cell population.

14. The method of claim 12, wherein the cell population added into each individual chamber is the same cell population.

15. The method of claim 12, wherein adding culture media to the well, further comprises separately adding culture media to each of the individual chambers so that the media is only in the bottom portion of the well.

16. The method of claim 15 wherein the culture media added to each individual chamber is the same culture media.

17. The method of claim 16, wherein the method further comprises adding a different treatment compound to each chamber.

18. The method of claim 15 wherein the culture media added to each individual chamber is a different culture media.

19. The method of claim 12, wherein adding culture media to the well, comprises, adding the media to the entire well in a volume that overfills the bottom portion of the well.

* * * * *